(12) United States Patent
Soudagar

(10) Patent No.: US 11,284,787 B2
(45) Date of Patent: Mar. 29, 2022

(54) MINIATURE MULTI-TARGET OPTICAL IMAGING APPARATUS

(71) Applicant: Neurescence, Inc., Toronto (CA)

(72) Inventor: Yasaman Soudagar, Toronto (CA)

(*) Notice: Subject to any disclaimer, the term of this patent is extended or adjusted under 35 U.S.C. 154(b) by 1138 days.

(21) Appl. No.: 15/329,831

(22) PCT Filed: Aug. 4, 2015

(86) PCT No.: PCT/CA2015/050731
§ 371 (c)(1),
(2) Date: Jan. 27, 2017

(87) PCT Pub. No.: WO2016/019458
PCT Pub. Date: Feb. 11, 2016

(65) Prior Publication Data
US 2017/0245747 A1 Aug. 31, 2017

Related U.S. Application Data

(60) Provisional application No. 62/033,150, filed on Aug. 5, 2014.

(51) Int. Cl.
A61B 1/07 (2006.01)
A61B 1/04 (2006.01)
(Continued)

(52) U.S. Cl.
CPC .............. A61B 1/07 (2013.01); A61B 1/00 (2013.01); A61B 1/00016 (2013.01);
(Continued)

(58) Field of Classification Search
USPC .................................................. 600/300–301
See application file for complete search history.

(56) References Cited

U.S. PATENT DOCUMENTS 5,261,410 A * 11/1993 Alfano ................. A61B 5/0075
250/339.12
5,926,592 A * 7/1999 Harris ................ G02B 21/0032
385/33

(Continued)

FOREIGN PATENT DOCUMENTS

EP 1580586 A1 9/2005
WO 03055379 A2 7/2003

OTHER PUBLICATIONS

Kristen Lantz Reichenbach and Chris Xu, "Numerical analysis of light propagation in image fibers or coherent fiber bundles," Opt. Express 15, 2151-2165 (2007), https://www.osapublishing.org/oe/fulltext.cfm?uri=oe-15-5-2151&id=130571, viewed on Sep. 11, 2021.*

(Continued)

Primary Examiner — Nathan J Jenness
Assistant Examiner — James Moss
(74) Attorney, Agent, or Firm — Benoit & Côté Inc.

(57) ABSTRACT

A multiple target optical imaging apparatus performs optical imaging of a plurality of physically-separated imaging sites using a light source, a two-dimensional detector and a plurality of fiber bundles. Each fiber bundle has a distal end positioned adjacent to a different one of the imaging sites, and conveys source light from its proximal end to its distal end, while conveying an optical signal from its respective imaging site from its distal end to its proximal end. The optical signals may be simultaneously detected on different regions of the detector. The system is small, and may be used to image sites on an ambulatory animal, with the light source and detector located in a portable housing attached to the animal. Different types of imaging may be used, including fluorescence imaging, hyperspectral imaging, or polarization imaging.

13 Claims, 20 Drawing Sheets

(51) Int. Cl.
| | |
|---|---|
| *A61B 1/00* | (2006.01) |
| *A61B 1/055* | (2006.01) |
| *F21V 8/00* | (2006.01) |
| *G02B 6/293* | (2006.01) |
| *G02B 6/06* | (2006.01) |
| *G02B 6/27* | (2006.01) |
| *G02B 6/42* | (2006.01) |
| *G02B 21/12* | (2006.01) |
| *G02B 21/36* | (2006.01) |

(52) U.S. Cl.
CPC ...... *A61B 1/00032* (2013.01); *A61B 1/00167* (2013.01); *A61B 1/04* (2013.01); *A61B 1/043* (2013.01); *A61B 1/055* (2013.01); *G02B 6/0006* (2013.01); *G02B 6/06* (2013.01); *G02B 6/276* (2013.01); *G02B 6/293* (2013.01); *G02B 6/4298* (2013.01); *G02B 21/12* (2013.01); *G02B 21/361* (2013.01)

(56) References Cited

U.S. PATENT DOCUMENTS

| | | | | |
|---|---|---|---|---|
| 6,437,856 | B1* | 8/2002 | Jacques | G01J 4/00 356/338 |
| 6,643,071 | B2* | 11/2003 | Schnitzer | G02B 21/02 359/368 |
| 7,023,622 | B2* | 4/2006 | Liang | G02B 21/02 359/660 |
| 7,450,243 | B2* | 11/2008 | Marks | A61B 5/0066 356/479 |
| 8,194,123 | B2* | 6/2012 | Iddan | H04N 5/2252 348/76 |
| 2005/0123303 | A1* | 6/2005 | Guttman | G01J 3/0218 398/142 |
| 2005/0267340 | A1* | 12/2005 | Ishihara | A61B 5/14552 600/310 |
| 2008/0204551 | A1* | 8/2008 | O'Connell | H04N 5/2251 348/79 |
| 2008/0231803 | A1* | 9/2008 | Feldon | G03B 3/02 351/206 |
| 2008/0262359 | A1* | 10/2008 | Tearney | A61B 1/00167 600/476 |
| 2011/0059016 | A1* | 3/2011 | Ramanujam | A61B 5/0059 424/9.1 |
| 2012/0302892 | A1* | 11/2012 | Lue | A61B 5/0071 600/476 |
| 2014/0336465 | A1* | 11/2014 | Demers | A61B 1/06 600/176 |
| 2014/0378845 | A1* | 12/2014 | Nadkarni | A61B 5/6853 600/478 |
| 2015/0148626 | A1* | 5/2015 | Sella-Tavor | A61B 5/0071 600/314 |
| 2015/0173619 | A1* | 6/2015 | Zvuloni | G01B 9/02083 600/425 |
| 2015/0282749 | A1* | 10/2015 | Zand | A61B 5/0071 600/301 |
| 2016/0022119 | A1* | 1/2016 | Shahmoon | G02B 23/26 600/182 |
| 2019/0382301 | A1* | 12/2019 | Stone | C03B 37/01214 |
| 2020/0394791 | A1* | 12/2020 | Pang | G06N 3/04 |
| 2021/0007585 | A1* | 1/2021 | Gill, IV | G02B 23/2469 |

OTHER PUBLICATIONS

Kunal K Ghosh et al. Miniaturized integration of a fluorescence microscope, nature methods, vol. 8 No. 10, Oct. 2011, 871.*
Christoph J. Engelbrecht et al. Ultra-compact fiber-optic two-photon microscope for functional fluorescence imaging in vivo. Optics Express, vol. 16, Issue 8, pp. 5556-5564 (2008) hitp://dx.doi.org/10.1364/OE.16.005556.*
Juergen Sawinski et al. Visually evoked activity in cortical cells imaged in freely moving animals. PNAS Nov. 17, 2009 vol. 106 No. 46 19557-19562 4.*
Isabelle Ferezou et al. Visualizing the Cortical Representation of Whisker Touch: Voltage-Sensitive Dye Imaging in Freely Moving Mice. Neuron 50, 617-629, May 18, 2006. DOI 10.1016/j.neuron.2006.03.043.*
Benjamin Flusberg et al. Fiber-optic fluorescence imaging. Nat Methods 2, 941-950 (2005). https://doi.org/10.1038/nmeth820.*
Metamouse. Introduction to Anticancer Inc. http:/www.metamouse.com/OV100%20brochure. pdf.*
Ronald S. Weinstein et al. An array microscope for ultrarapid virtual slide processing and telepathology. Design, fabrication, and validation study, Human Pathology, vol. 35, Issue 11, 2004, pp. 1303-1314, ISSN 0046-8177, https://doi.org/10.1016/j.humpath.2004.09.002.*
Kester et al. Real-time snapshot hyperspectral imaging endoscope. J. of Biomedical Optics, 16(5), 056005 (2011). https://doi.org/10.1117/1.3574756.*
Lawrence Livermore National Laboratory. In vivo Imaging of Tissue Microstructures & Cells, https://ipo.llnl.gov/technologies/life-sciences-biotech-and-healthcare/vivo-imaging-tissue-microstructures-cells.*
The mobile microscope, Nature Methods 7, 9 (2010) doi:10.1038/nmeth0110-09.*
Alencar et al., "Novel Multiwavelength Microscopic Scanner for Mouse Imaging", Neoplasia, pp. 977-983, vol. 7, No. 11, Nov. 2005.
Engel et al., "Dual-channel spectrally encoded endoscopic probe", Biomedical Optics Express, pp. 1855-1864, vol. 3, No. 8, Aug. 1, 2012.
Flusberg et al., "Fiber-optic fluorescence imaging", Nature Publishing Group, pp. 941-950, vol. 2, No. 12, Dec. 2005.
Liu et al., "Review Article: Modern Trends in Immagng II, Point-of-care pathology with miniature microscopes", Analytical Cellular Pathology 34, pp. 81-98, 2011.
Oh et al., "Optical fibers for high-resolution in vivo microendoscopic fluorescence imaging", Optical Fiber Technology, 2013.
Santos et al., "Optically sectioned fluorescence endomicroscopy with hybrid-illumination imaging through a flexible fiber bundle", Journal of Biomedical Opticas, pp. 030502-1 to 030502-3, vol. 14(3), May/Jun. 2009.

* cited by examiner

MINIATURE MULTI-TARGET OPTICAL IMAGING APPARATUS

BACKGROUND OF THE INVENTION

Field of the Invention

The present matter relates generally to an optical imaging device and, more specifically, to a miniaturized optical imaging device for in vitro or in vivo imaging.

Description of the Related Art

Throughout the years, the need for imaging biological tissue in vivo for applications ranging from neuronal imaging to imaging cells to differentiate cancer cells from normal cells has increased. Various optical imaging devices exist for these purposes, examples of which are a miniature free space microscope for fluorescence imaging of neurons in a live, freely moving mammal, and example of which is shown in FIG. 1. A device such as this is described in *Miniaturized Integration of a Fluorescence Microscope*, Kunal K. Ghosh et al., Nature Methods, Vol. 8 No. 10, October 2011, p. 871, which is incorporated herein by reference. This device uses a graded index lens 121 (known as a GRIN lens) to both illuminate and collect light from the object. A light emitting diode (LED) 160 is used to illuminate the object, while a lens 153 couples the LED light into the GRIN lens 121. An illumination filter 155 and an emission filter 170 make sure the light that arrives at the detector 180 is only the light that fluoresced from the object. A lens 141 completes the imaging onto the detector 180. Both LED 160 and detector's electronics 190 are powered by connections 163 and 191 to external DC voltage supplies and the detector also transmits images to a computer using a wire connection 191.

Another type of device, as described, for example, in *Ultra-compact Fiber-optic Two-photon Microscope for Functional Fluorescence Imaging in vivo*, Christoph J. Engelbrecht et al., Optics Express, Vol. 16, Issue 8, pp. 5556-5564 (2008) and in *Visually Evoked Activity in Cortical Cells Imaged in Freely Moving Animals*, Juergen Sawinski et al., PNAS, Nov. 17, 2009, vol. 106, No. 46, pp. 19557-19562, allows multi-photon absorption imaging in a freely moving mammal.

Yet, another example, as described in *Neuron* 50, 617-629, May 18, 2006, Elsevier Inc., uses a coherent fiber bundle for in vivo fluorescence imaging of a small mammal, as the mammal moves around freely.

Various imaging techniques using an optical fiber are summarized in *Fiber-optic Fluorescence Imaging*, Benjamin A Flusberg, Eric D Cocker, Wibool Piyawattanametha et al., Nature Methods, Vol. 2 No. 12, December 2005. Other examples exist of various optical imaging devices and modalities that are used for biological imaging.

SUMMARY OF THE INVENTION

In accordance with the present invention, a multiple target optical imaging apparatus is provided that performs optical imaging of a plurality of physically-separated imaging sites. The apparatus includes at least one light source for illuminating the imaging sites, and a two-dimensional detector. A plurality of fiber bundles each have a proximal end and a distal end, such that the distal end of each bundle is positioned adjacent to a different one of the imaging sites. Each fiber bundle conveys light generated by the light source from the proximal end to the distal end of the bundle, and each conveys an optical signal from a respective imaging site from its distal end to its proximal end.

In one embodiment of the invention, the optical signal from each fiber bundle is directed to a different spatial region of a detection surface of the detector. The detector may also be configured such that it detects all of the optical signals simultaneously. In a particular application, the plurality of imaging sites includes different imaging locations on a biological subject, such as an animal. The different imaging sites may correspond to a plurality of different biological systems of the animal, which may be conscious and ambulatory. To adapt the system to the animal, the light source and detector may be located in a portable housing attached to the animal's body. Batteries may be used as a power source for the system, and a wireless transceiver can be used to communicate data collected by the detector to a remote location.

Different variations of the invention may also have features that adapt it to a specific application. For example, at least one of the fiber bundles may include a magnification element that provides magnification of the optical signal received from the respective imaging site for that bundle. In another embodiment, a wavelength dispersive element may be used that separates the optical signal from at least one of the fiber bundles into discrete wavelength ranges. In a different embodiment, the system may use a polarization-dependent filter that filters the optical signal of at least one of the fiber bundles. In yet another embodiment, the optical signal of at least one of the fiber bundles is a fluorescence signal.

Depending on the configuration of the light source, detector and fiber bundles, as well as the specific application in question, different components may be used for controlling the light entering and exiting each of the fiber bundles. For example, a dichroic mirror may be used to provide separation of light from the light source from the optical signal from one or more of the imaging sites. Similarly, a beamsplitter may be used to provide wavelength-independent separation of the light from the light source and/or one or more of the optical signals. Lenses may also be used in different positions in the system to allow proper focusing and/or collimation of light entering or exiting the fiber bundles, or being directed from the light source or toward the detector. A plurality of such lenses may also be used, with each lens being associated with one of the fiber bundles.

BRIEF DESCRIPTION OF THE DRAWINGS

In order that the subject matter may be readily understood, embodiments are illustrated by way of examples in the accompanying drawings, in which.

DETAILED DESCRIPTION

Figure 1:
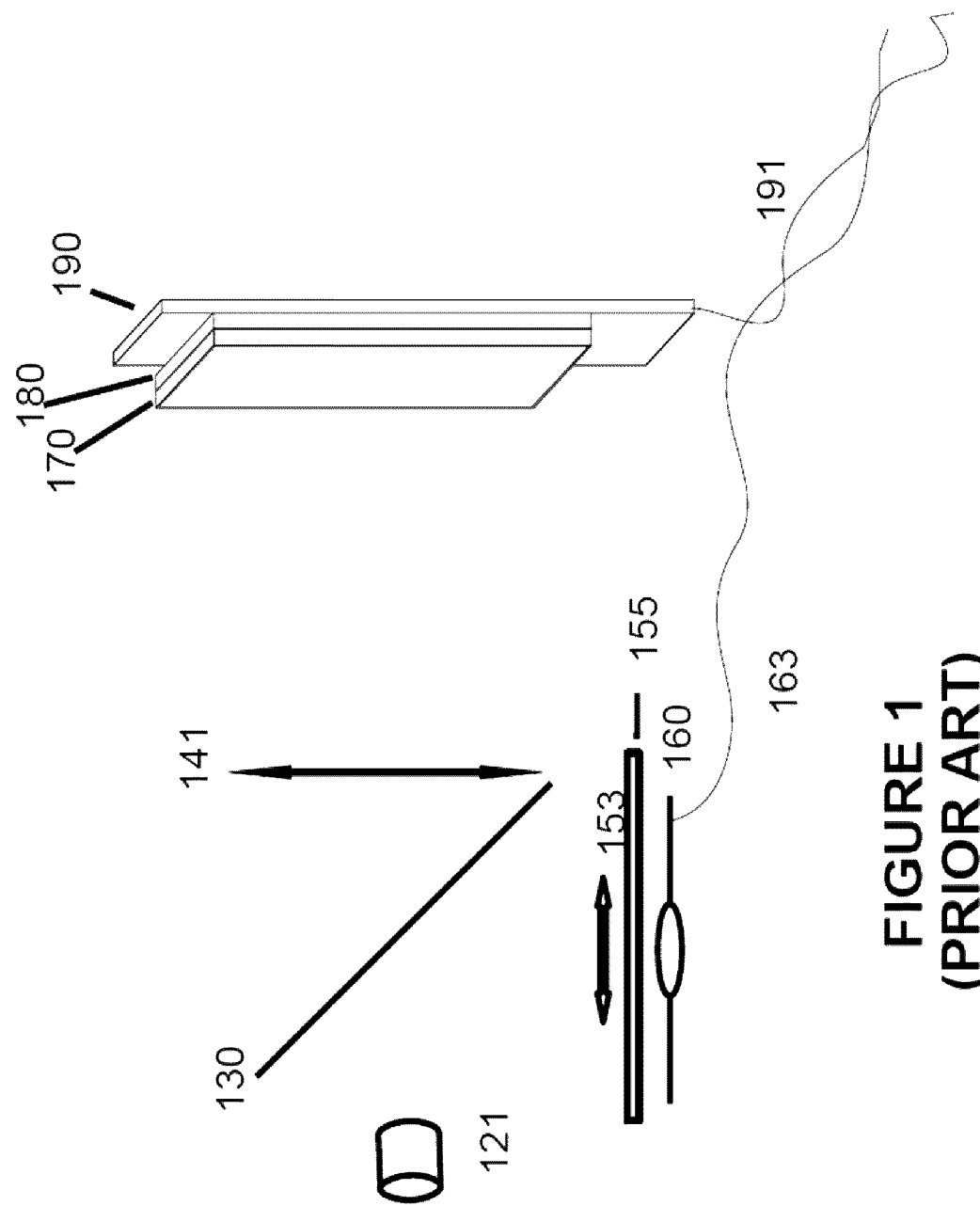
FIG. 1 is a schematic view of a miniature free space microscope according to the prior art.
Figure 2:
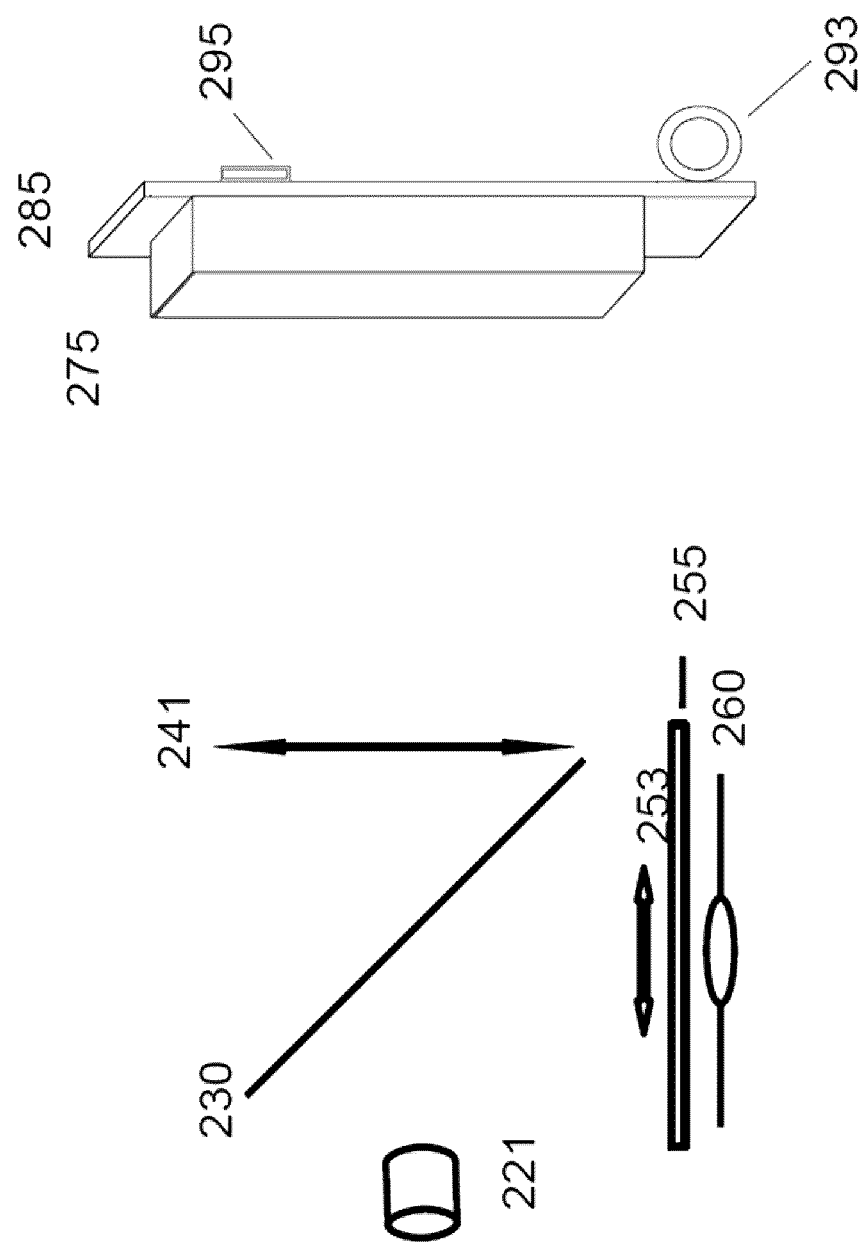
FIG. 2 is a schematic view of a hyperspectral imaging arrangement for one imaging site.

The basic principles of a one region hyperspectral imager are shown schematically in FIG. 2. As in the prior art arrangement shown in FIG. 1, the FIG. 2 system uses a GRIN lens 221 to both illuminate and collect light from an object. LED 260 is used to illuminate the object, with lens 253 coupling the LED light into the GRIN lens 221 via dichroic mirror 230. Lens 241 is used to project the image returning from the object on the combination of filter 275 and detector 285. Unlike the prior art, which uses a regular detector, the filter, or dispersive element 275 is used to separate the light into frequency blocks that are detected, respectively, in different regions of detector 285. A micro SD slot 295 may also be connected to the detector to allow images to be saved locally on a micro SD card if the device is not connected to a computer. In addition, the detector 285 may be configured to communicate with a computer through a wireless connection 293.

Figure 10:
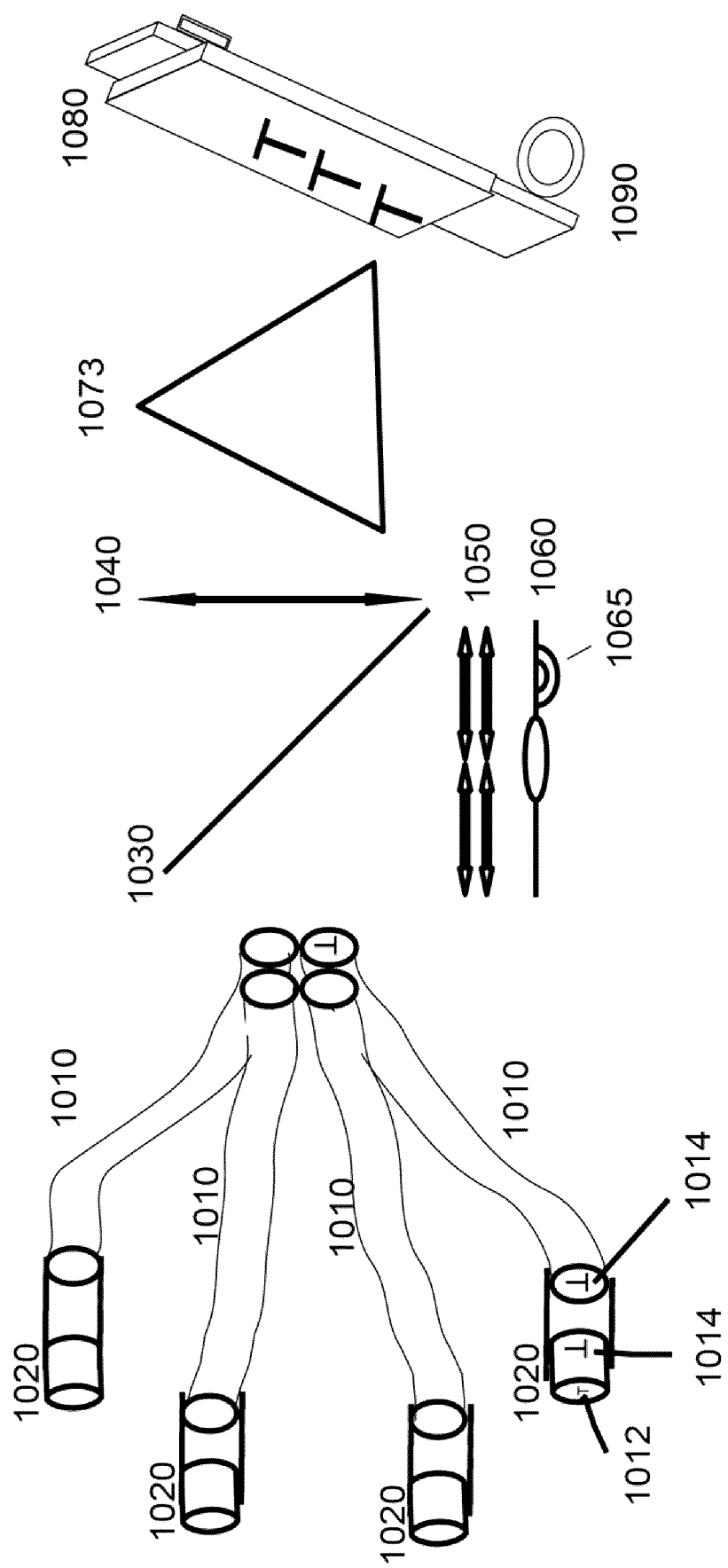
FIG. 10 is a schematic view of an alternative embodiment of the invention for use with hyperspectral imaging.

For certain applications, the dichroic mirror 230 may be replaced by a broadband 50:50 beamsplitter, and the LED 260 may be a flat white LED. Those skilled in the art will understand that the hyperspectral imaging technique can be used to simultaneously detect more than one wavelength of light, and that one can use multiple color tags, such as different fluorescent proteins, and use excitation LEDs for these tags and a proper dichroic mirror that reflects the illumination wavelengths and transmits the emitted ones. If such a dichroic mirror for the range of wavelengths is not used, one can use the full hyperspectral imaging setup, i.e., a 50:50 beamsplitter instead of the dichroic mirror and a flat-white LED for illumination. In a variation of this embodiment, the lens 241 properly focuses the beam coming out of GRIN lens 221 to form an image on the detector and a detection arrangement as shown in FIG. 10 is used, which is discussed in more detail below.

Figure 3:
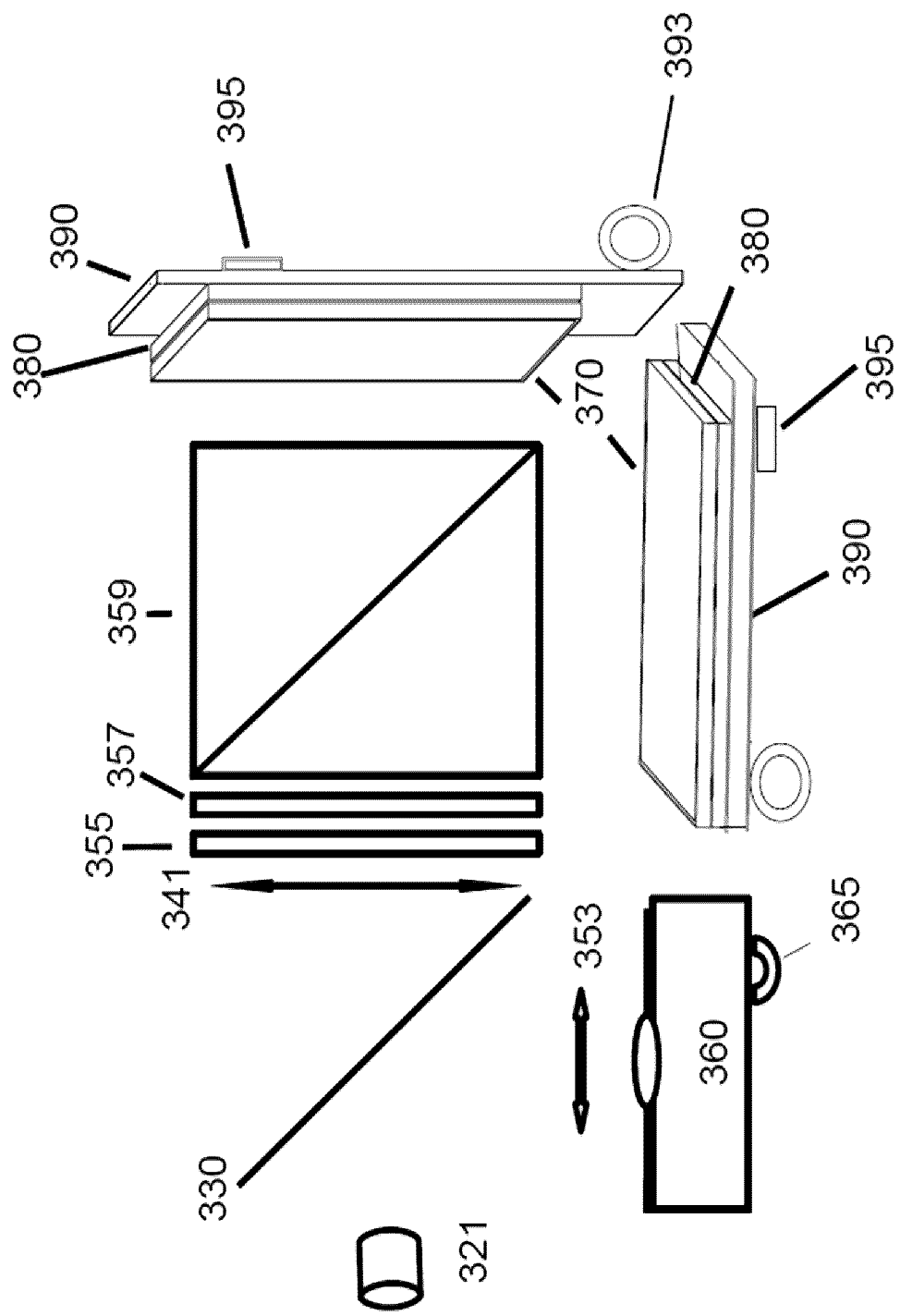
FIG. 3 is a schematic view of one example of polarization imaging of one imaging site.

FIG. 3 shows another configuration that may be used for polarization imaging. A more detailed explanation of the polarization imaging is provided below. Unlike the embodiment of FIG. 2, that shown in FIG. 3 uses a quarter-wave plate 355 and half-wave plate 357, as well as a polarization beamsplitter cube 359 to separate the light returning from the sample according to its orthogonal polarization states after it passes through the dichroic mirror 330 and is focused by lens 341. Each separated light signal is thereafter directed to a respective filter 370 and detector 380 combination. If a full ellipsometry technique is desired, that is, the type of polarization imaging that allows finding the amount of birefringence of the object, an illumination source may be used that generates polarized light, such as a laser. In such a case, it is important to know the direction of polarization of the illumination when it arrives at the object and to make sure to keep that direction constant. Also shown in the figure is a small power source in the form of one or more micro-batteries 365, and support electronics 390 for each of the detectors 380. A small wireless transceiver 393 may also be used to provide wireless connection of the device to a host computer, as well as a micro SD card slot 395 to allow local data storage.

Figure 4:
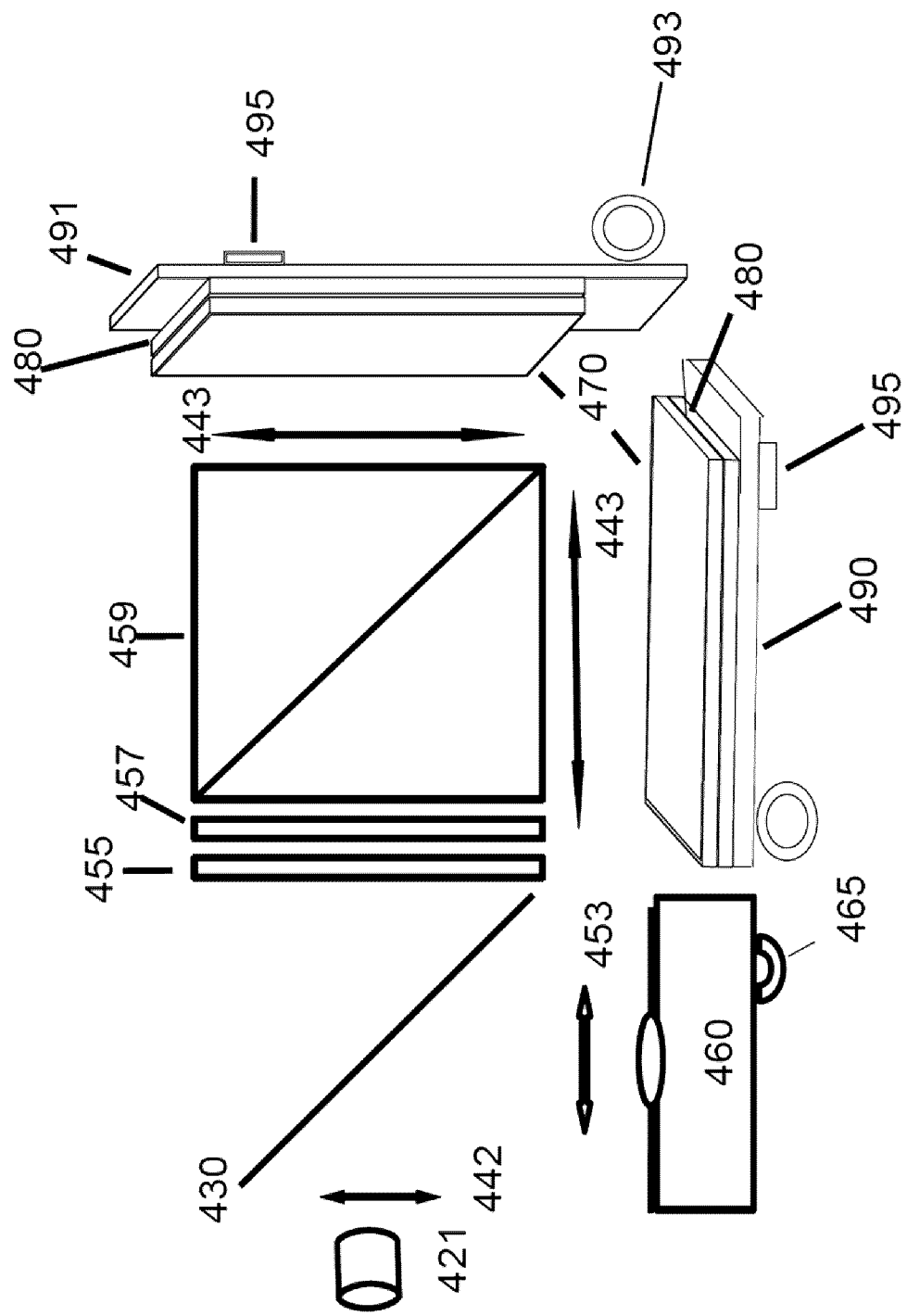
FIG. 4 is a schematic view of an alternative type of polarization imaging of one imaging site.

FIG. 4 shows another adaptation for polarization imaging, where lens 442 collimates the light exiting the GRIN lens, which then passes through polarization optics including quarter-wave plate 455, half-wave plate 457, and polarization beamsplitter cube 459, as in the embodiment of FIG. 3. Each of the separated light beams is then directed to a respective one of two lenses 443 that images the beam onto its respective detector 480. In this design, all rays of light enter the polarization optics at the proper angle, i.e., orthogonal to the surface of the polarization beamsplitter cube 459 and, thus, the polarization image has better fidelity or polarization extinction. This adaptation can also be used with the multi-region imaging technique that is described below and shown in FIGS. 12 and 13. As with the embodiment of FIG. 3, a small battery 465 may be provided for local system power. Also as shown in previous embodiments, a micro SD card slot 495 may be provided, along with a wireless transceiver 493.

The miniature multiple site imaging system can be used to simultaneously obtain images from multiple imaging sites, and may be used to image multiple hard-to-reach regions. In the example below a biomedical imaging usage is discussed. For example, the instrument can be used to image neurons in a number of brain regions of a mammal as small as a mouse, as well as a number of places on the spine and in the muscles of the mammal all simultaneously. In one embodiment, the device can present a global view of the brain function and its circuitry, and how it is connected to the rest of the nervous system and bodily functions. The presented device is versatile and allows multi-region in vivo imaging with single-cell resolution of various imaging types, such as bright field microscopy, fluorescence microscopy, confocal microscopy, hyperspectral microscopy, polarization microscopy and multi-photon absorption microscopy.

Figure 5:
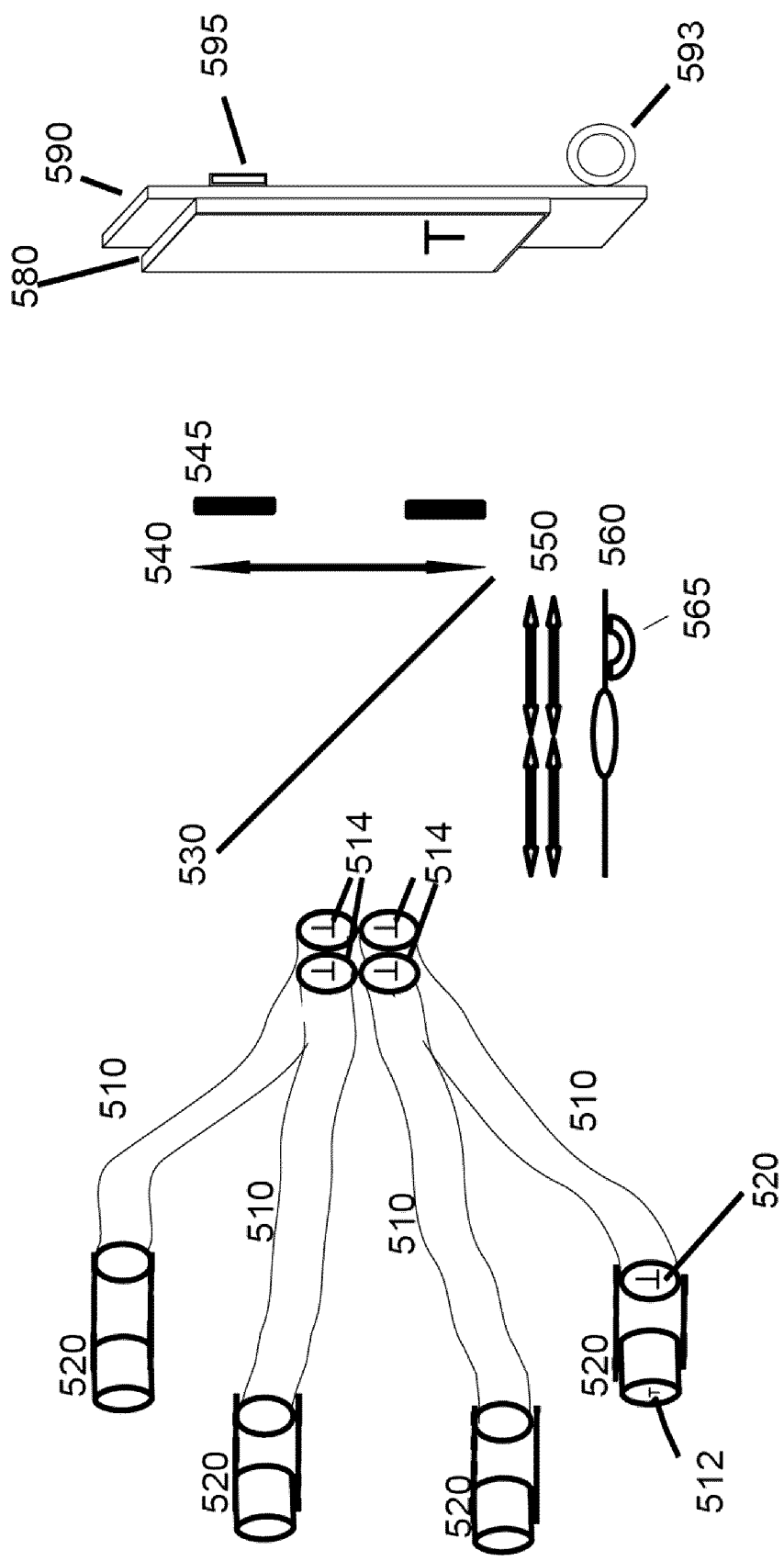
FIG. 5 is a schematic view of an embodiment of the invention for use with bright field imaging.

FIG. 5 shows an embodiment of a miniature microscope according to the present invention that is optimized for bright field microscopy. The device consists of multiple coherent fiber bundles 510, four of which are shown in the figure as an example. These bundles are used to illuminate the object and also to collect the light returning from the object (i.e., collect the image) and to transfer the image to the rest of the optical device.

Any number of fiber bundles can be used as long as the resolution of the detecting film or electronic detector 580 allows the image features to be extracted. This is because the area of the detector is fixed, and as one adds to the number of fiber bundles, it is necessary to change the distance between the lens 540 and the detector 580 to image all images at the ends of all fiber bundles 510 at the detector. At some point the images might be too small to occupy enough pixels of the detector to allow the extraction of information. In such a case, one should reduce the pixel size, increase the detection region or reduce the number of fiber bundles.

An object 512 is imaged into the fiber bundle either directly, or by using a magnifier 520, such as a GRIN lens or a half ball lens, or a micro-compound lens. The magnifier projects a magnified image of the object 512 on the surface of the coherent fiber bundle. The bundle then transfers the image intact to its other end 514. Depending on the type of the magnifier used, the magnifier might be placed either right at the end of the fiber bundle or might be placed at some distance from it.

For any of the embodiments described herein, one can use different magnifiers for different coherent fiber bundles. For example, one might want to use one of the fiber bundles to image a portion of the nervous system that requires a larger field of view. This can be achieved by using the proper magnifier 520 that gives the required field of view for this coherent fiber bundle, while one might use a different magnifier 520 for another coherent fiber bundle for imaging a different region that achieves higher magnification and a smaller field of view. This flexibility significantly increases the versatility of the disclosed invention.

The illumination source 560 may be an LED of a certain wavelength range, or a laser or white light source the output of which is transmitted to the location at which element 560 is shown using another coherent bundle. Such a "source" coherent bundle is not used in the imaging part of the apparatus. For bright field microscopy it is preferable to use white light such as the output of a flat white LED that has a relatively uniform power spectrum across the visible range of the electromagnetic spectrum. As in previous embodiments, such an LED can be powered by a tiny battery 565, possibly one that can be recharged in a wireless manner.

Figure 6:
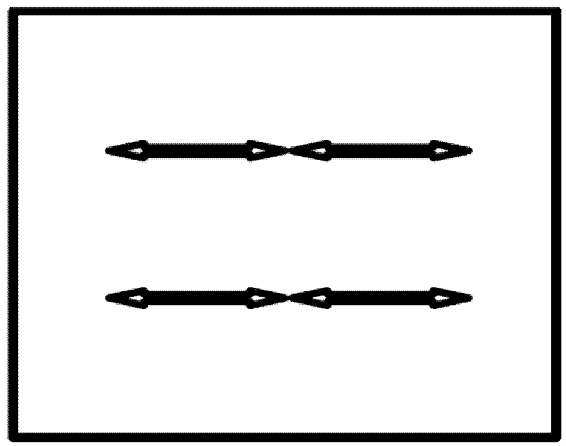
FIG. 6 is a schematic view of a lens array for use with the imaging embodiment of FIG. 5.

An array of convex micro lenses 550, with the number of lenses being equal to the number of coherent bundles, or an LED-beam shaper or a diffraction grating if a laser is used for illumination, is used to divide the illumination beam into multiple beams, focus the beams and direct each into its respective coherent fiber bundle via dichroic mirror 530. The array of micro lenses is arranged in the same configuration as the bundles to allow for spatial correspondence between the lenses and the fiber bundles. For example, if four fiber bundles are arranged in a two-by-two array of square shape, as shown in FIG. 5, the lenses will have the same configuration. A possible spatial arrangement of lenses 550 is shown schematically in FIG. 6, and a corresponding arrangement of the ends of fiber bundles is shown schematically in FIG. 7.

Figure 7:
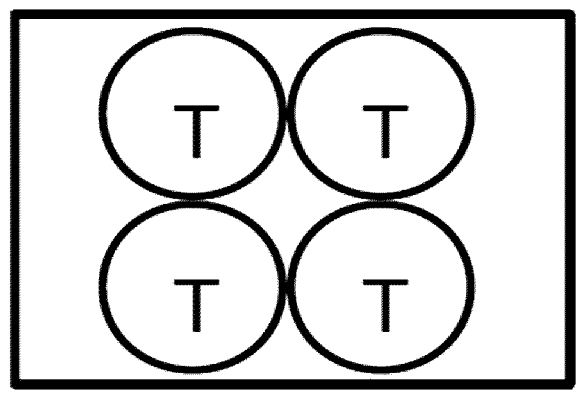
FIG. 7 is a schematic view of an arrangement of fiber bundles that may be used with the embodiment of FIG. 5.

Referring again to FIG. 5, the dichroic mirror 530 is used to reflect the illumination beam into the coherent fiber bundles. Depending on the specific application, the dichroic mirror can be replaced by a 50:50 beamsplitter. A convex lens 540 is used to image the plane of coherent fiber bundles, containing the signals returned from the various imaging regions, onto detector 580. For four fiber bundles, the image received by the detector will be of the ends of the four bundles, such as is shown in FIG. 7. As shown in FIG. 5, an aperture 545 of a size smaller than the diameter of the lens 540 may also be used to eliminate any stray light arriving at the detector.

The detector 580 is connected to an electronic board 590 that may be configured to communicate with a computer through a wireless connection 593. Such a wireless connection is particularly useful when imaging a live, ambulatory subject, such as a mouse. This allows the subject (e.g., a mouse), to move around with no constraints whatsoever. In a variation of this embodiment, a micro SD slot 595 is provided to allow images to be saved locally on a micro SD card if the device is not connected to a computer. Small batteries that can be charged wirelessly can be used to power such an electronic board. Similarly, the illumination LED 560 and corresponding electronics board can be powered by wirelessly rechargeable micro batteries 565 or, alternatively, by a physical connection to a DC power supply and/or computer USB port.

For the purpose of imaging neurons in the brain, for each coherent fiber bundle, the magnifier 520 is set into a cylinder made of biocompatible material, such as stainless steel, with an inner diameter that matches the outer diameter of the coherent fiber bundle tip. The cylinder is secured in an annular support plate that can be made of plastic. The annular plate supports the cylinder and resides at the surface of the brain in contact with the skull. Using screws connecting the plate to the skull and dental cement, the plate is thus secured relative to the skull to make sure the cylinder, and thus the magnifier, cannot move. The coherent fiber bundle is then inserted into the cylinder and screwed in place. This method of implantation with the cylinder-plate arrangement can be used for all imaging techniques outlined below.

Figure 8:
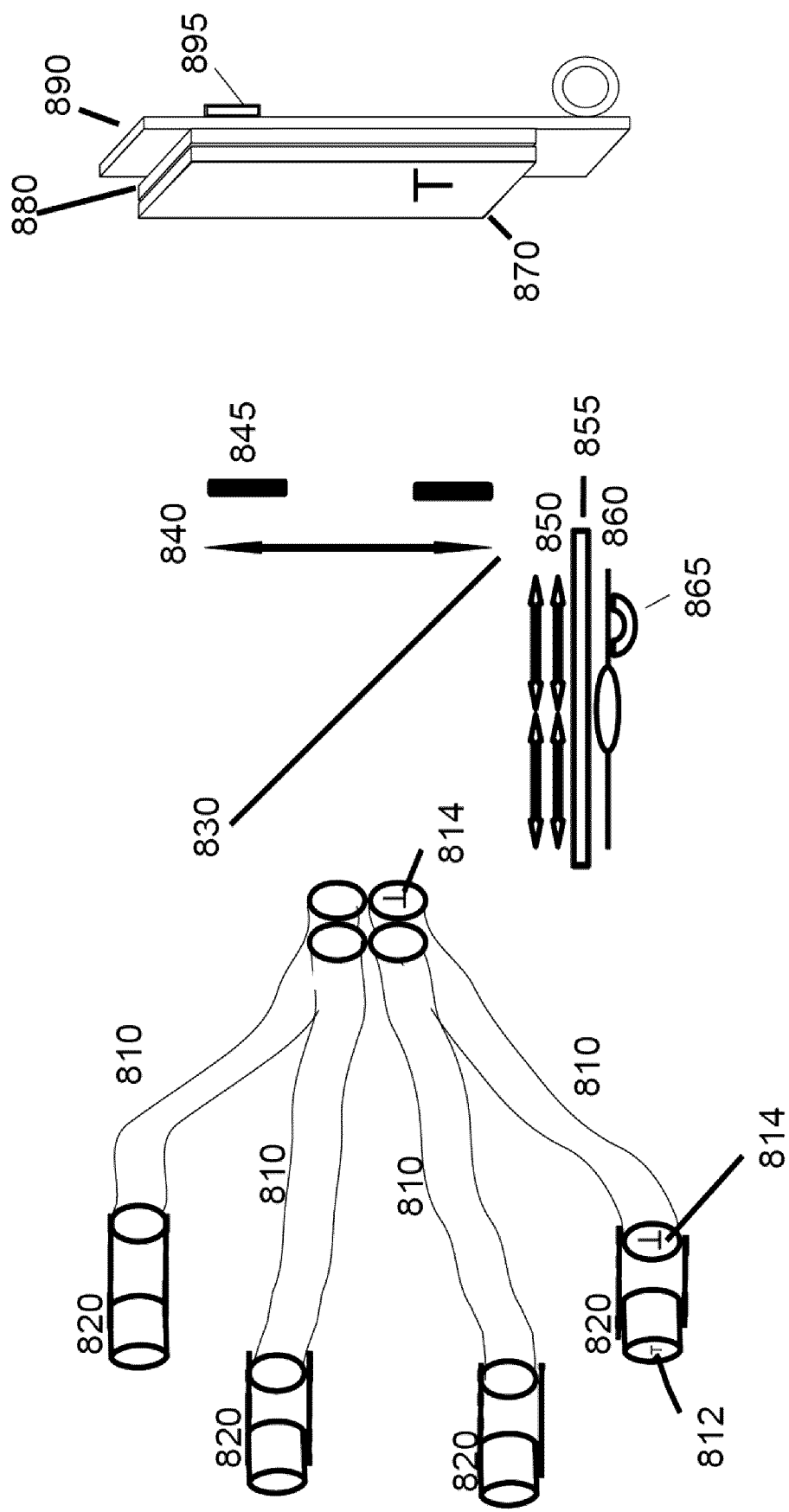
FIG. 8 is a schematic view of an embodiment of the invention that may be used for fluorescent microscopy.

FIG. 8 shows an embodiment of the invention for use with fluorescence microscopy. This embodiment is similar to that of FIG. 5, but the illumination source is chosen such that its wavelength excites the type of fluorophores that are to be imaged. For example, if one is using the Ds Red-Express protein, the maximum excitation happens at 554 nm and maximum emission happens at 586 nm. Hence, an LED 860 may be used that has a high power close to 554 nm in its spectrum. In order to minimize the overlap between the illumination and emission spectrum, it may be preferable to choose an LED 860 with its peak emission at a wavelength shorter than 554 nm, e.g., at 535 nm, and to use a filter 855 adjacent to the LED 860 that transmits the range of wavelengths of (535+/−20) nm. This filter may be located either before or after the lens array 850. Another filter 870 at the collection side, having a transmission range 560 nm to 650 nm, may be used to limit the range of wavelengths that arrive at the detector to the wavelength emission range of the protein of interest. This filter 870 can be placed anywhere between lens 840 and detector 880.

Figure 9:
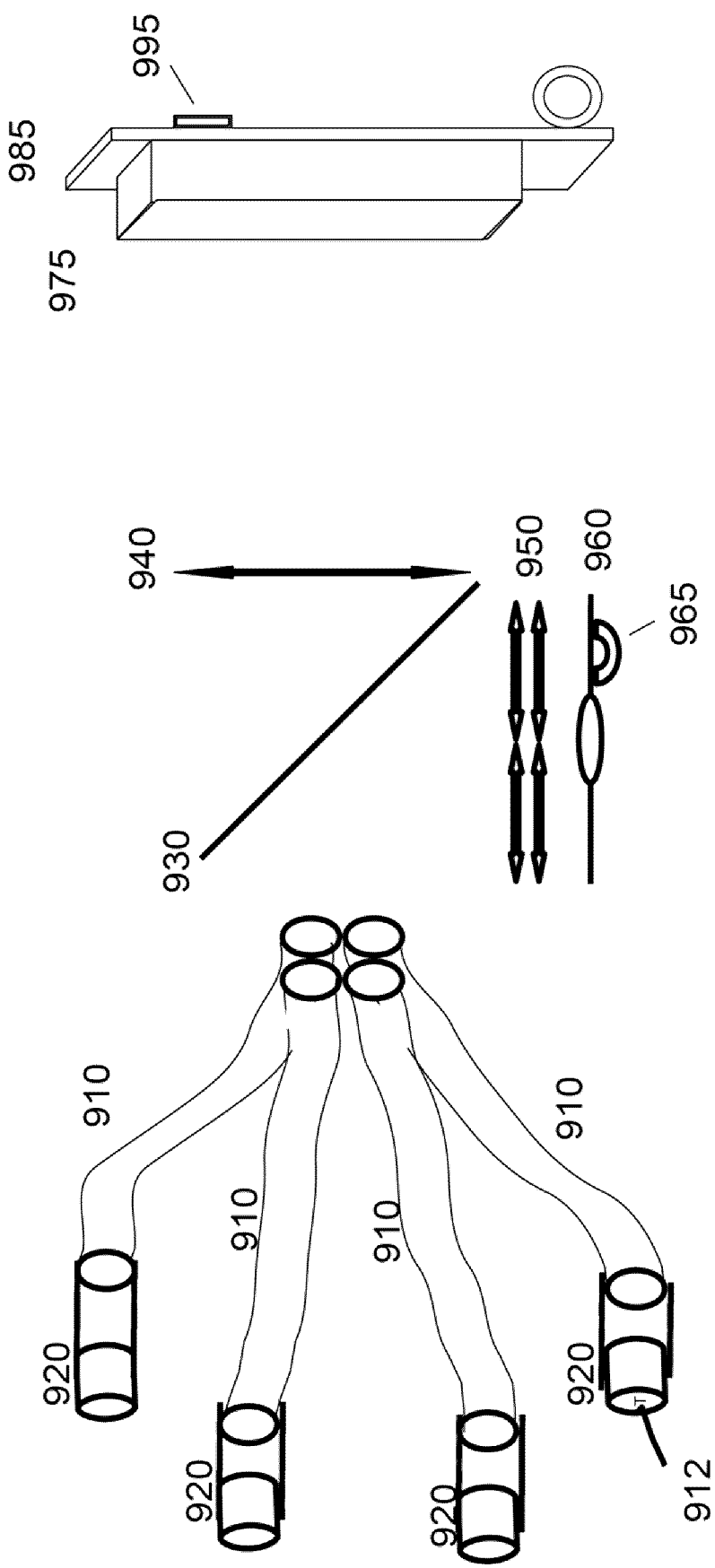
FIG. 9 is a schematic view of an embodiment of the invention that may be used for hyperspectral imaging.
Figure 11:
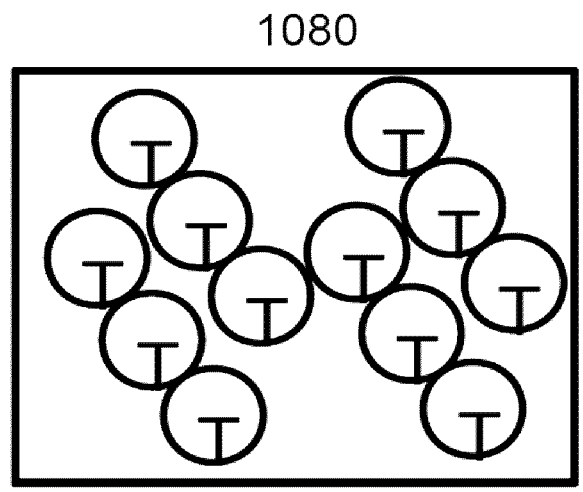
FIG. 11 is a schematic view of the face of the detector of the FIG. 10 embodiment, with an example of the arrangement of the image of different spectral components from fiber bundles.
Figure 17D:
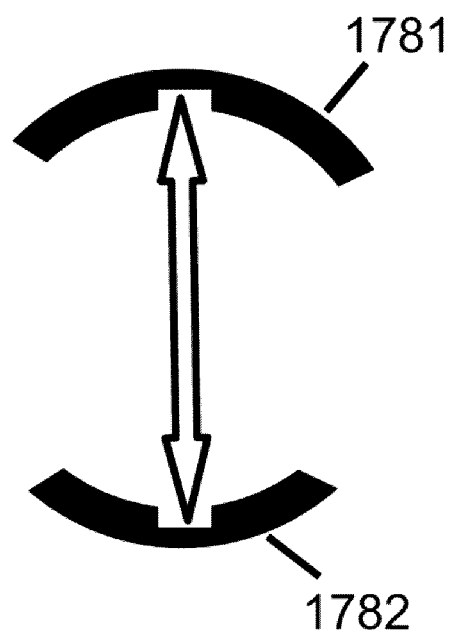
FIG. 17D is a schematic view of a portion of the housing arrangement of FIG. 17A that holds a projecting lens.

FIG. 9 and FIG. 10 show, respectively, two different arrangements for hyperspectral imaging. In each of these embodiments, the illumination source (960, 1060) is white light, either from a flat white LED or from a source for which the light is brought to the site using a coherent fiber bundle. No filters are used after illumination, as in hyperspectral imaging the image is decomposed into its various frequency components. This is done with some form of dispersive element that can separate the various frequencies either in time or space. An example of a dispersive element that does this separation in space is the prism 1073 shown in FIG. 10. To make the image more comprehensible, in this example the white image is divided into three frequency ranges, referred to as red, green and blue. Hence, for each fiber bundle in this embodiment, there are three images on the detector face as shown in FIG. 11. In this case, the detector must be selected to have a detection surface large enough to accommodate all of the images. The example of FIG. 11 shows a configuration for four coherent fiber bundles, which can be achieved using the correct orientation of the prism and detector.

Other examples of dispersive elements include a diffraction grating for spatial dispersion or an optical element such as a non-linear crystal that introduces a frequency dependent phase change. For the latter, each frequency can be accessed by measuring the phase shift.

In the FIG. 9 example, a combination of a detector 985 and a special filter 975 is used. The filter 975 separates the frequency components of the image into a number of frequency intervals at various blocks of pixels. This combination of filter and detector is then connected to an electronic processing unit that saves the images on a micro SD card 995 or transfers them to a computer, as described above with regard to other embodiments.

Figure 12:
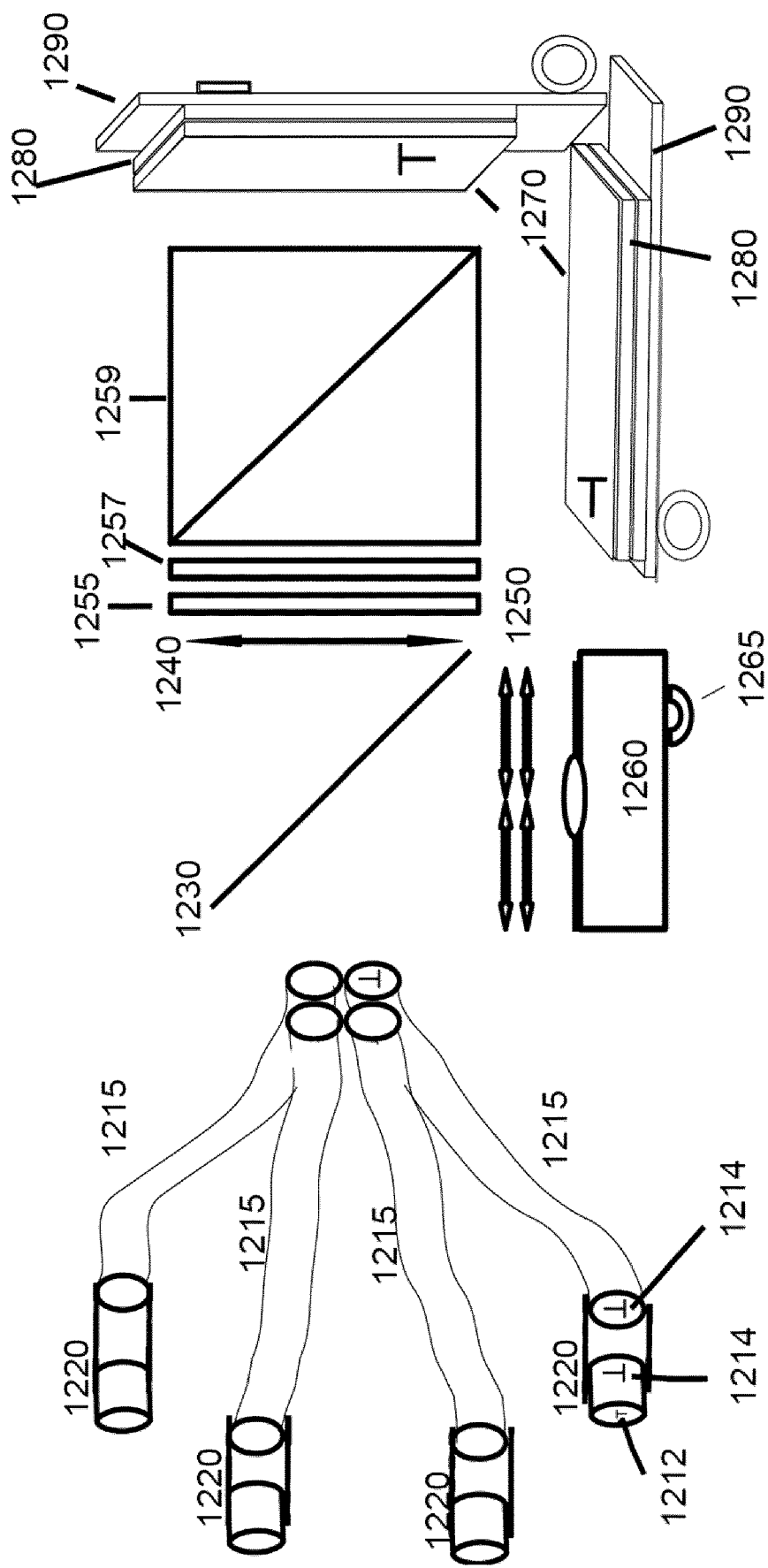
FIG. 12 is a schematic view of an embodiment of the invention that may be used for polarization imaging.

An embodiment of the invention for use with polarization imaging is shown in FIG. 12. If one wants to measure the birefringence of the material that is being imaged, it is necessary to use light with a certain polarization relative to the object and to measure how the object changes the polarization. For this, a polarized illumination source should be used, such as a laser diode 1260. Regular coherent fiber bundles do not preserve the polarization, hence this embodiment uses polarization maintaining coherent fiber bundles 1215. Care must also be taken to make sure the dichroic mirror 1230 will not affect the polarization. As the rotation of a fiber bundle also changes the polarization with respect to surrounding reference frame, system must be arranged to avoid any such polarization change. A polarization tomography at the output of each bundle may be used to verify the polarization of illumination light and thereby allow for any deviations to be corrected. During imaging, care should be taken to use the bundle in the correct orientation.

In the FIG. 12 embodiment, light from the laser diode 1260 passes through lens array 1250 and is reflected by dichroic mirror 1230 into the fiber bundles 1215. Light exiting the fiber bundles via magnifiers 1220 illuminates the imaging sites. The optical signals returning from the imaging sites are collected by the fiber bundles and, after passing through dichroic mirror 1230 and lens 1240, arrive at a polarization tomography setup, which includes a quarter-wave plate 1255, a half-wave plate 1257 and a polarization beamsplitter 1259. This combination can project the beams into the basis set equivalent to the standard horizontal/vertical, diagonal/anti-diagonal and left/right polarization, or the Stokes vectors. The beams separated by the polarization beamsplitter each pass a respective filter 1270 on route to a detector 1280. The filters 1270 block stray light and, if one only wants to do polarization imaging, they may be narrowband laser line filters that transmit the same wavelength as the source 1260. However, if one wants to combine polarization with other imaging modalities, such as bright field or fluorescence imaging, the appropriate filters, as described in the aforementioned embodiments, may be used.

To obtain better polarization extinction, it is possible to use a lens right after the fiber bundles to fully collimate the beams coming out of these fibers. In such a case, lens 1240 may be eliminated, and additional lenses after the polarization beamsplitter cube 1259 may be used to project the image onto the two detectors. This would be similar to the arrangement shown in FIG. 4.

Another variation of this embodiment makes use of an unpolarized illumination source, such as an LED like those discussed above for fluorescence or hyperspectral imaging. However, in this version, the image is viewed with multiple polarizations. Thus, one may use either full polarization tomography or a measurement in only one polarization basis set to obtain information about the object that is being imaged. In this manner one can easily obtain bright field or fluorescence or hyperspectral images and the polarization all at the same time with no more change to those setups than just adding the quarter-wave plate 1255, half-wave plate 1257 and the polarization beamsplitter 1259, as shown in FIG. 12.

Figure 13:
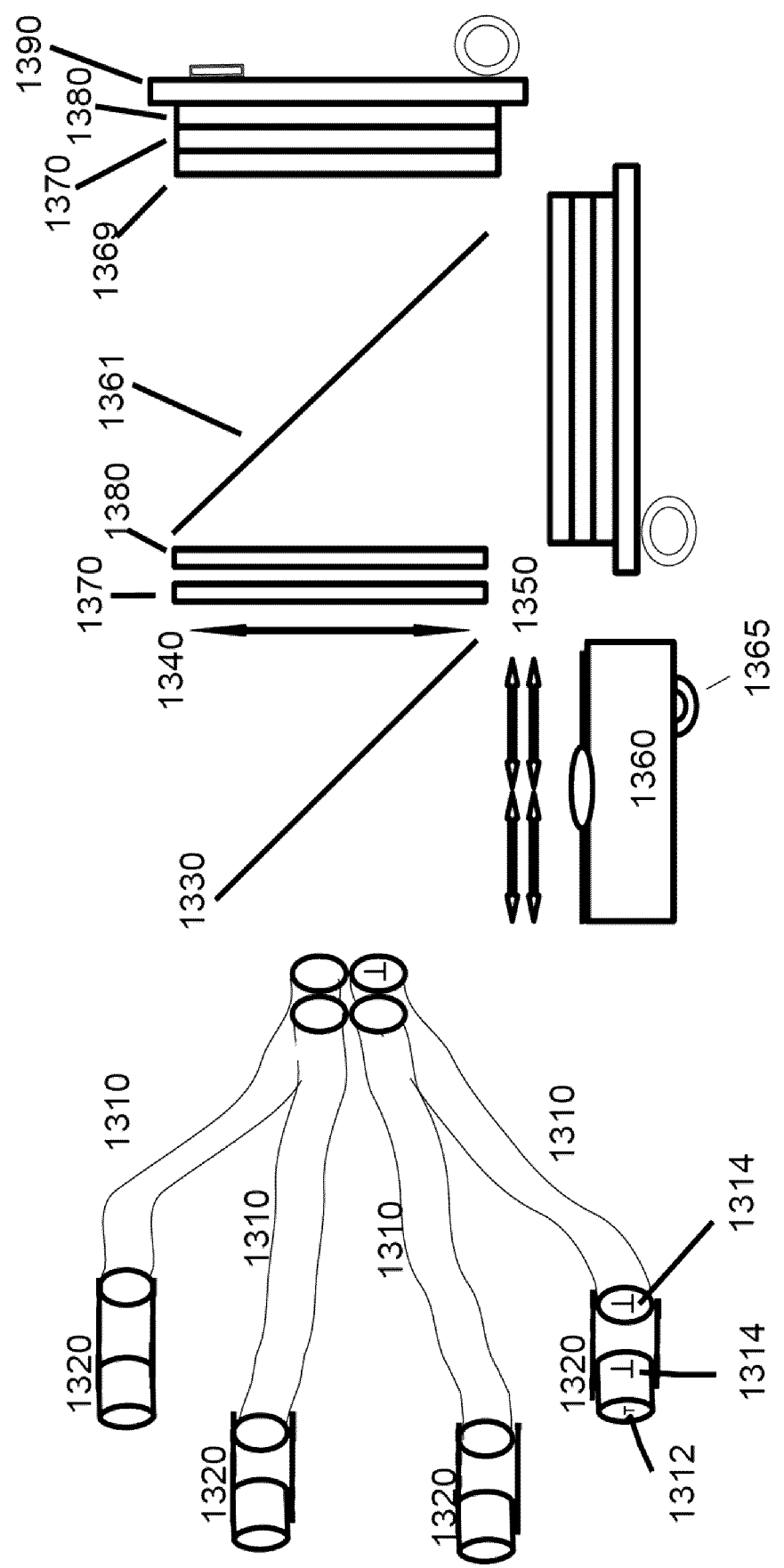
FIG. 13 is a schematic view of an alternative embodiment of the invention that may be used for polarization imaging.

FIG. 13 shows another adaptation of the device for polarization measurement similar to that of FIG. 12. However, in this adaptation the polarization beamsplitter is replaced by a 50:50 beamsplitter 1361, and polarizers 1369 are added in front of the filter 1370 and detector 1380 combination. The polarizers are set in the device such that they each pass a different orthogonal polarization. For example, if the polarizer encountered by light transmitted through the beamsplitter 1361 allows horizontally polarized light to go through it, the one encountered by light reflected by the beamsplitter 1361 allows only vertically polarized light to go through it. In this way, the polarization-specific nature of the two detectors is preserved.

Figure 14:
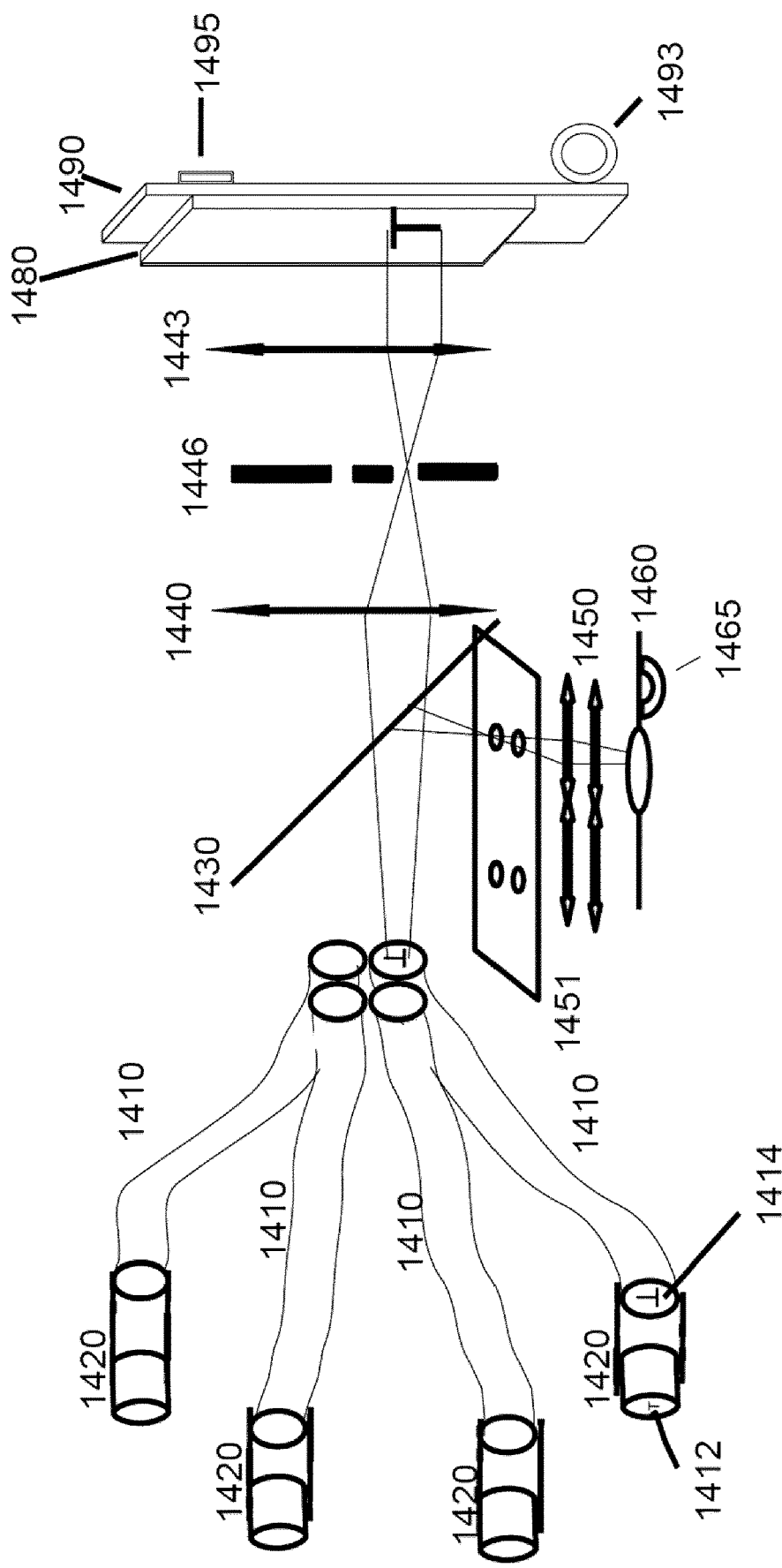
FIG. 14 is a schematic view of an embodiment of the invention that may be used for confocal imaging.

FIG. 14 shows an adaptation of the invention for confocal imaging. Confocal imaging uses pinholes at the focal point of a beam to block the light that is not focused at the same location. In this embodiment, it is the light that is emitted from each target location that is focused on its respective pinhole. This improves the final image by increasing the signal to noise ratio. In the examples shown in FIG. 14, four lenses with focal length about 1 mm are arranged in a lens array configuration 1450 and situated at about 2 mm from the light source. A screen 1451 with four 1 mm diameter apertures is set at about 2 mm from the lens array 1450. Ray tracing for one of the lenses of the lens array 1450 shows how light from light source 1460 passes through one of the lenses in the lens array and subsequently through one of the pinholes of the screen 1451. This represents only one of the illuminating beams and, when it is reflected by the dichroic mirror 1430, it enters one of the fiber bundles 1410. The beam returning from the imaged object is collected by the same fiber bundle and is transmitted through the dichroic mirror 1430. A lens 1440 focuses the beam through one of the pinholes of a screen 1446. For example, if a focal length of lens 1440 equals 3 mm, a screen 1446 with four apertures of 1 mm is placed at a distance of about 4.5 mm from the lens 1440. Another lens 1443 having a focal length of 3 mm, is located about 3 mm from the screen 1446 and collimates the beam onto the detector 1480. Those skilled in the art will recognize that the dimensions used herein are by way of example only, and that other sizes and configurations may also be used.

Figure 15:
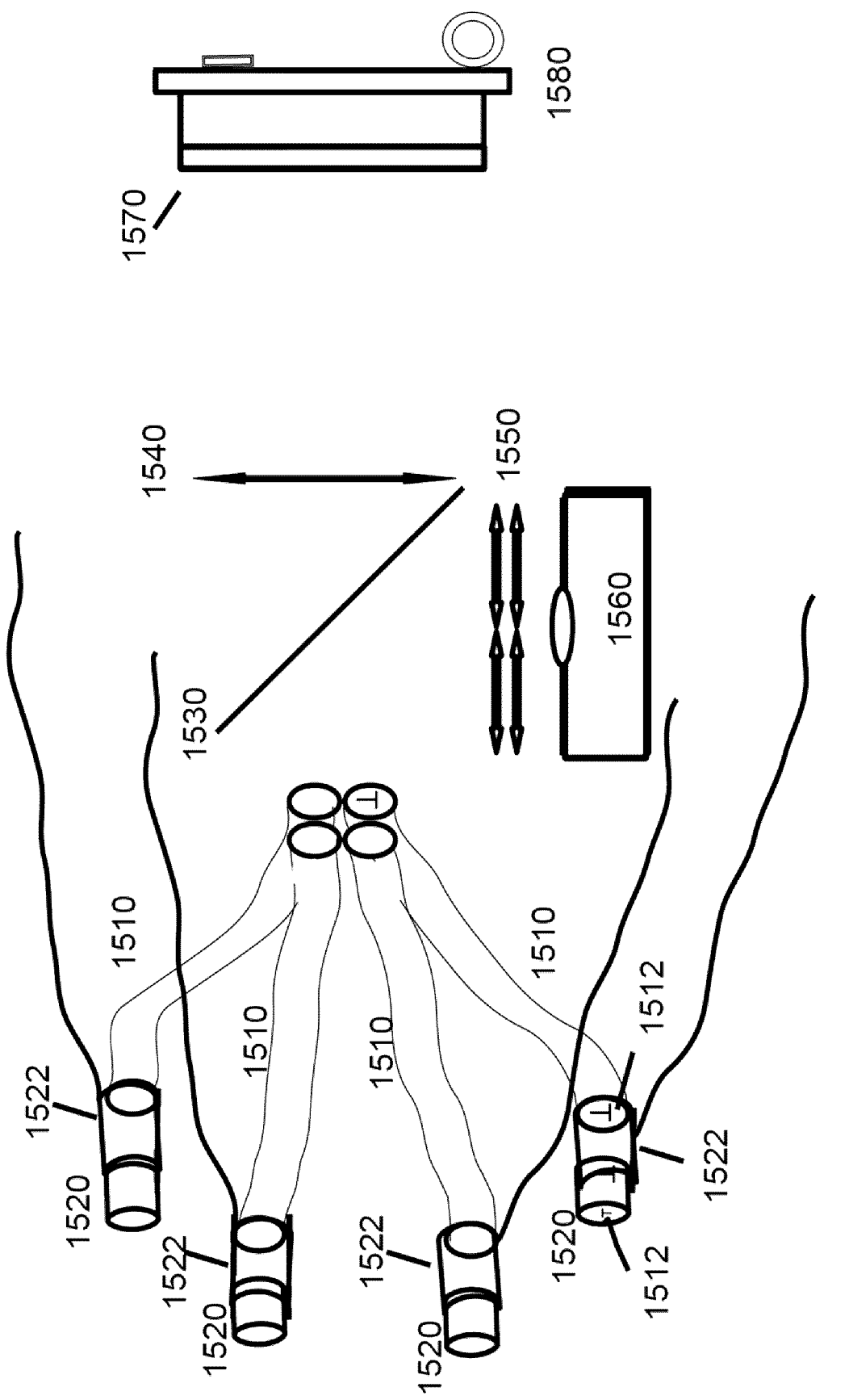
FIG. 15 is a schematic view of an embodiment of the invention that may be used for multiphoton absorption imaging.

FIG. 15 shows an embodiment of the device for multiphoton absorption imaging. In this embodiment, the illumination source 1560 is a pulsed laser with short pulse duration, such that the peak power is high enough to give rise to the required non-linear effect, even after it is divided into multiple beams. Each beam is then delivered to its respective target using a coherent fiber bundle 1510 and is focused on the target with a magnifier 1520. Each magnifier is connected to its corresponding coherent bundle using a tube piezo electric modulator 1522 which scans the magnifier around and thus scans the laser beam. The photons emitted from the site are collected by the same coherent fiber bundle and delivered to filter 1570 and detector 1580 via dichroic mirror 1530 and lens 1540. In this embodiment, the detector 1580 is a photon sensitive detector, such as a single photon sensitive CCD or a photomultiplier tube. This type of imaging includes any multi-photon absorption or multi-photon non-linear effect, examples of which are Coherent Anti-Stokes Raman Spectroscopy (CARS) and Surface Enhanced Raman Spectroscopy (SERS). For any of these methods, one may change the wavelength of the source and adapt the dichroic mirror 1530. For example, to use CARS, one illuminates the sample with a certain laser wavelength, which depends on the material that is being imaged. The non-linear interaction of the material with the laser beam converts two photons of the illuminating laser beam, called the pump beam, to two other photons with different wavelengths, such that the energy and momentum are conserved. These two photons correspond to beams of light which are referred to, respectively, as Stokes and Anti-Stokes. One can choose to monitor either the change of intensity in the illumination beam or the change in one of the Stokes or Anti-Stokes beams. If monitoring the Stokes beam, for example, dichroic mirror 1530 is used to reflect the illumination beam and transmit the Stokes beam. Filters 1570 are thus chosen to be narrowband and to transmit only the Stokes beam. If one chooses to monitor the intensity of the reflected pump beam, a 50:50 beamsplitter is used instead of a dichroic mirror, and the filters 1570 are chosen to be narrowband and to transmit the same wavelength as the pump beam.

For Raman spectroscopy, the region of interest is illuminated with a single wavelength, e.g., from a laser beam. The photons from this beam interact with the molecules at the imaging site and exchange energy with the material, thereby undergoing a wavelength shift. The amount of energy exchanged, and therefore the magnitude of the wavelength shift, depends on the specific material. One skilled in the art will understand how to choose the proper laser wavelength to match the material they are imaging. When looking for a specific material, one knows the wavelength of the emitted photons from this material. Hence, element 1530 of FIG. 15 is a 50:50 beamsplitter to reflect the illuminating laser towards the fiber bundles and allow for all emitted wavelengths to transmit through to the filters 1570. These filters should be chosen to transmit only the wavelengths corresponding to the signature of the material of interest to the detection means 1580. For Surface Enhanced Raman Spectroscopy (SERS), one should use the appropriate gold, silver, or quantum dot nanoparticles at the site that is to be imaged, e.g., the brain tissue, to increase the probability of a pump photon interacting with the material of interest and resulting in an energy exchange between the pump beam and the tissue. This technique can be used in both CARS and Raman spectroscopy, without significantly changing the imaging apparatus.

Figure 16:
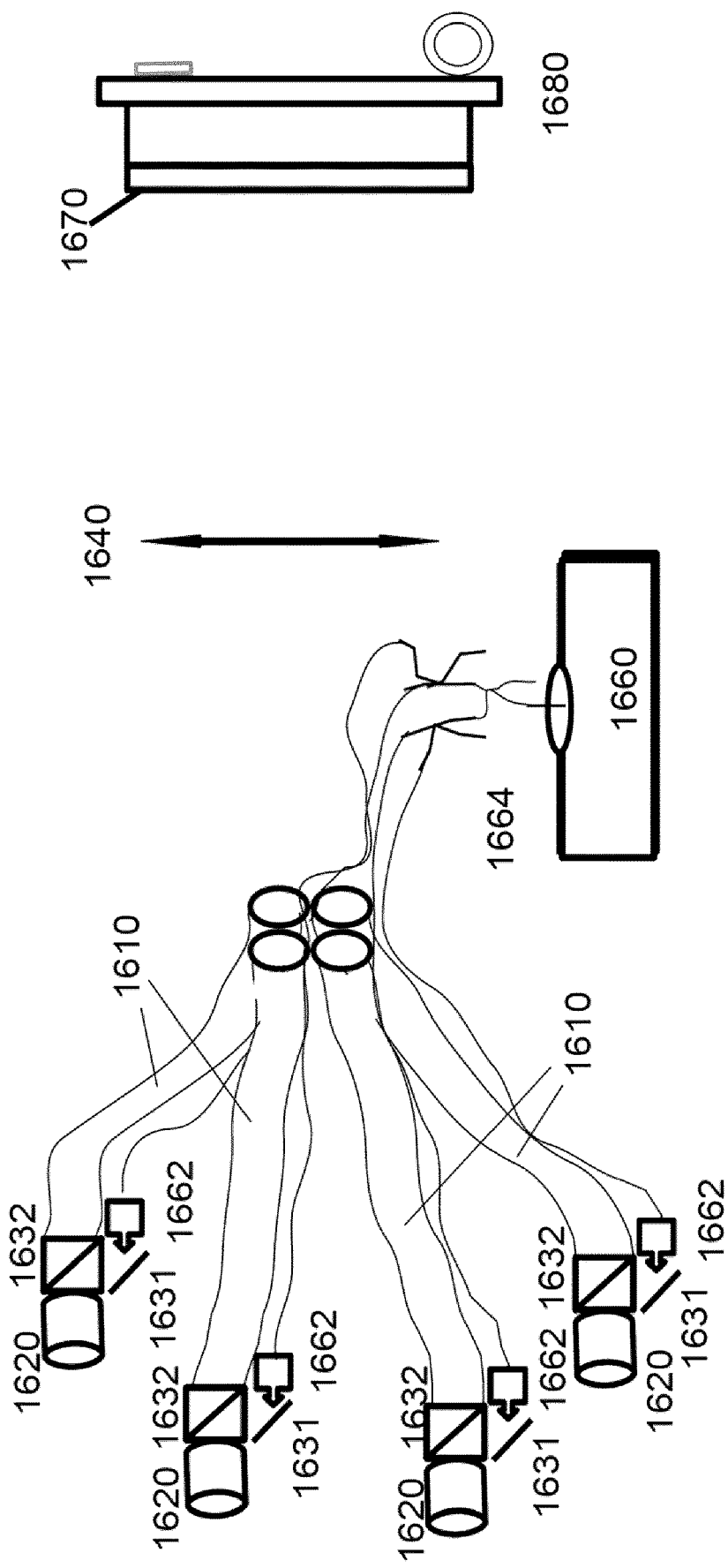
FIG. 16 is a schematic view of an alternative embodiment of the invention for use with multiphoton absorption imaging.

A different embodiment of the invention based on multi-photon absorption imaging is shown in FIG. 16. In this embodiment, laser light from the source 1660 arrives at an object being examined using a separate, single mode fiber, while the image returned from the object is collected by one of the coherent fiber bundles 1610. Hence, there is a single mode fiber associated with each imaging site that runs parallel to the coherent fiber bundle. The laser is coupled to the single mode fibers, whose number is the same as the imaging site numbers, using a 1-to-n switch or, for the example shown having four fiber bundles, a 1-to-4 fiber optical coupler or a succession of 50:50 fiber couplers 1664, as shown in the figure. The scanning of the light from each fiber across a desired range can be accomplished using MEMS mirrors 1631 at the imaging site. The light arriving at each MEMS mirror is transmitted by a respective single mode fiber from the laser source 1660, and directed onto the mirror 1631 by a collimation lens 1662. This source beam is at an illumination wavelength, and is reflected off the MEMS mirror 1631 toward a miniature dichroic mirror 1632. The dichroic mirror reflects the illumination wavelength, which is focused onto the sample by magnifier 1620, while the returning emission wavelength from the sample is collected by the magnifier 1620, transmitted through the dichroic mirror 1632 and coupled into the fiber bundle 1610. The image transferred to the final end of the fiber bundle is then projected onto the single photon sensitive detector 1680 via lens 1640 and filter 1670.

The invention can be adapted, and the various elements described can be combined, to allow for multi-modal imaging. For example, to make a device that combines fluorescence, polarization and hyperspectral imaging, one should use a polarized illumination source with the proper spectrum, which is both broadband and covers the excitation wavelength of the fluorophores, as is the case with the element 860 in the device described in FIG. 8. To be able to detect separated multiple wavelengths of the spectrum to obtain hyperspectral imaging, one replaces the detector 880 and its electronics 890 by device 975 and 985 of FIG. 9. With this method, the user not only sees the natural reflection of the various frequencies from the specimen, but also picks up the fluorescence signal from fluorophores. Thus, it is shown how both fluorescence and hyperspectral imaging may be accommodated. To include polarization imaging, one inserts the polarization measurement components, which include the elements 1370, 1380 and 1369 of FIG. 13 before device 975 and 985. A device made with the optical elements described above can simultaneously perform fluorescence, polarization and hyperspectral imaging.

For any realization of the device described above, one can use a housing that allows fine tuning of the device at time of use. One such design is shown in FIG. 17. All of the fiber bundles of a given configuration are brought together and secured in a cylinder 1702 that can slide in another cylinder 1704. After the optimal position is achieved, two screws 1706 are tightened to apply pressure over the surface of the inner cylinder and fix the two cylinders together. The optimal position for cylinder 1702 is where the spacing between the tips of coherent fiber bundles and the focusing lens is such that a clearly focused image is produced.

Figure 17A:
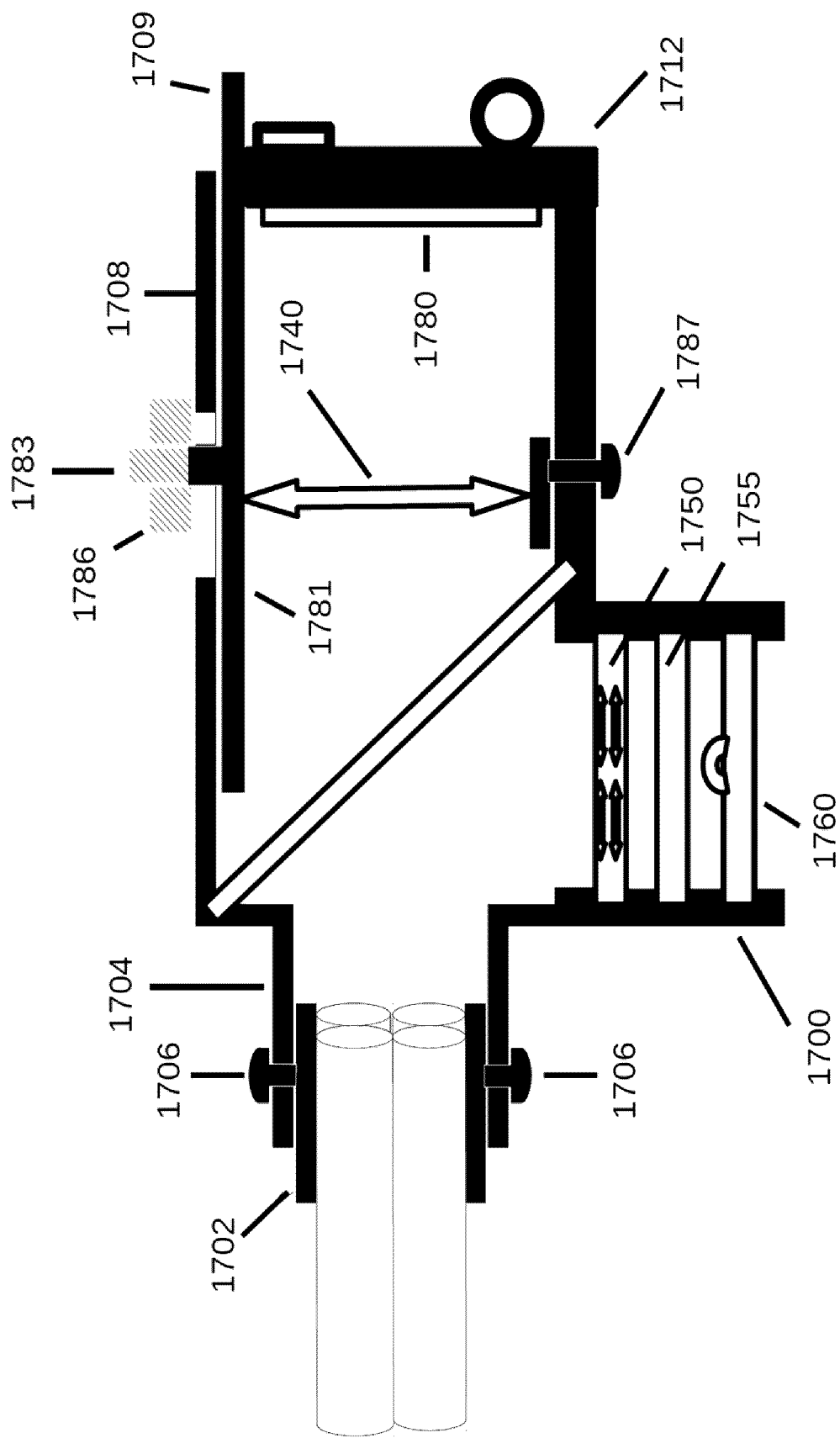
FIG. 17A is a schematic view of a housing arrangement for the present invention that allows fine optimization of the device for individual use.
Figure 17B:
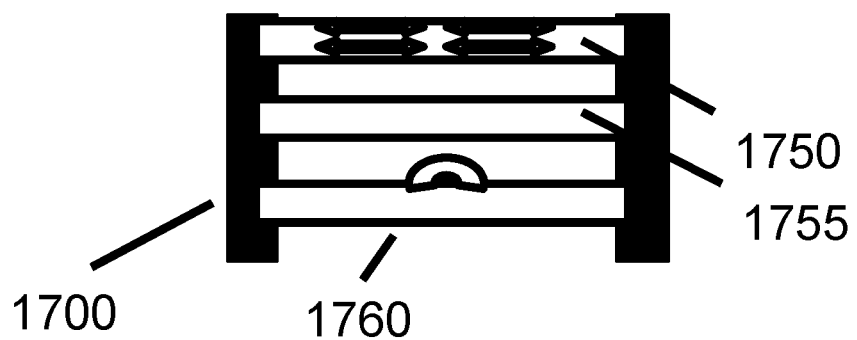
FIG. 17B is a schematic view of a portion of the housing arrangement of FIG. 17A for enclosing the illumination components.
Figure 17C:
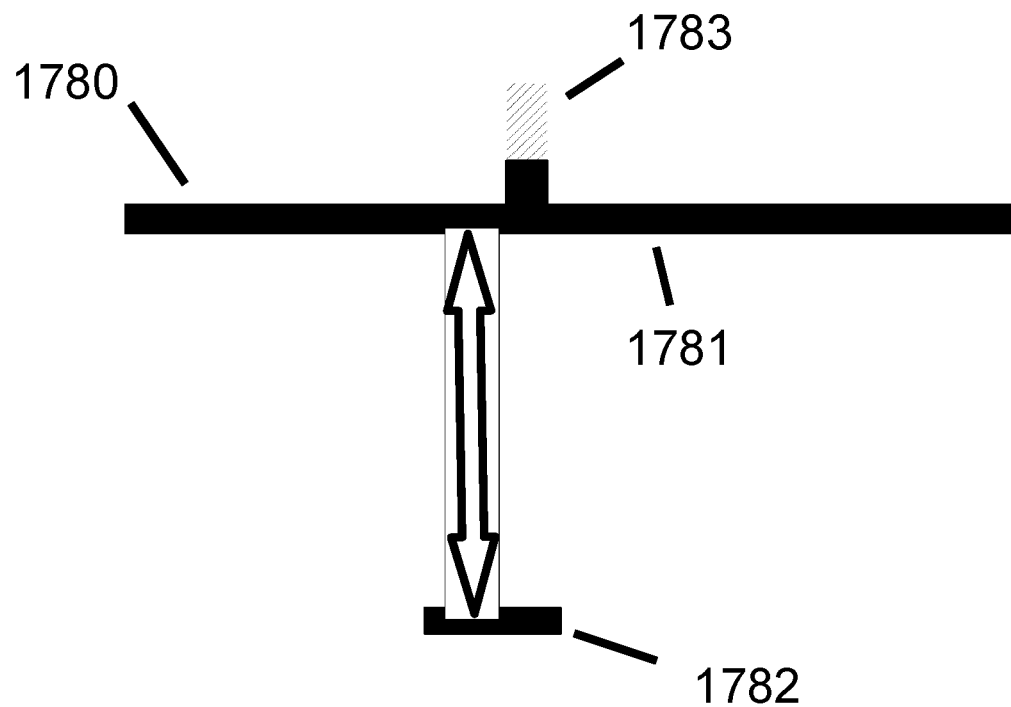
FIG. 17C is a schematic view of a portion of the housing arrangement of FIG. 17A that holds the lens that projects the image on the detector.

The housing 1700 holds the illumination source 1760, the filter 1755, and the lens array 1750 in place, details of which are shown in FIG. 17B. Cylinder 1708 is either fixed to cylinder 1704 or they are a monolithic piece. Support 1709 holds lens 1740 and can slide along a slot of length 6 mm and width 1 mm in cylinder 1708. This part includes a cylinder that holds the lens, and has a long narrow slider 1781 with total length of 23 mm, and height of 1 mm and width of 4 mm, as shown in FIG. 17C. A threaded handle 1783 extends from the slider 1781 and can accept a knot. It protrudes from the slot and allows the user to slide the slider along the slot. Once the components are assembled and adjusted, a knot 1786 fastens support 1709 in place, as shown in FIG. 17A. A set screw 1787 on the opposite side further strengthens support 1709 in place. Opposite to slider 1781 there is a similar component 1782, which is shown in FIG. 17C and has a smaller length of 8 mm. There are no slots on this side. The design is such that slider 1781 can protrude out of the cylinder 1708 adjacent to the detector system 1780. After all adjustments are done, this protruding piece can be cut to match the length of cylinder 1708. Finally, housing 1712 holds the filters and detection device. The parts can connect to each other either by glue or by tiny screws.

Figure 19A:
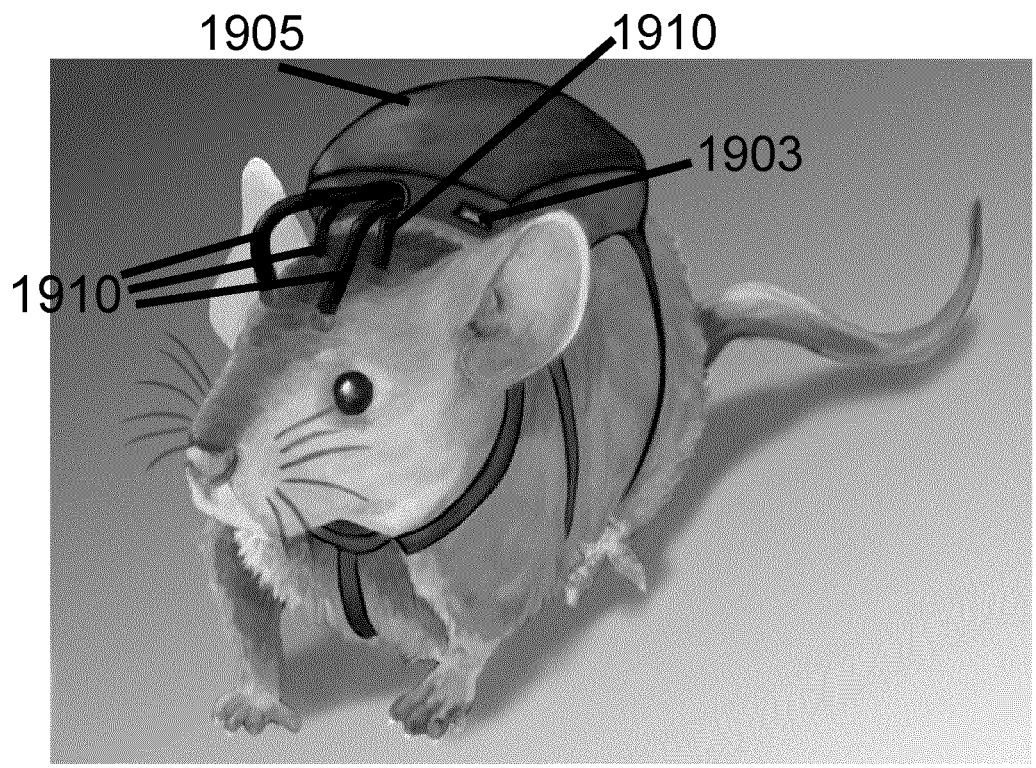
FIG. 19A is a graphical depiction of the use of the invention with a mouse.

One can also replace the second focusing means and the detection means by a small camera such as a cell phone camera. In this case one cannot completely separate the subject from the device, unless the subject carries the camera in a backpack 1905 as shown in FIG. 19A.

Figure 18A:
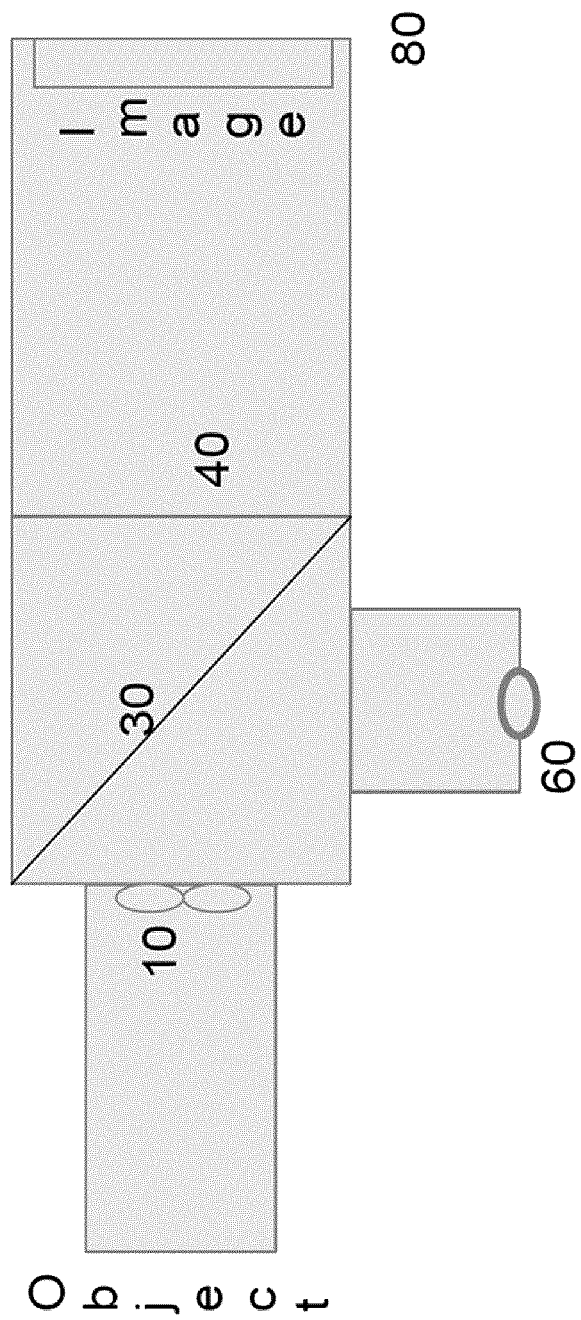
FIGS. 18A and 18B show schematically different geometrical configurations for the components of the present invention.
Figure 18B:
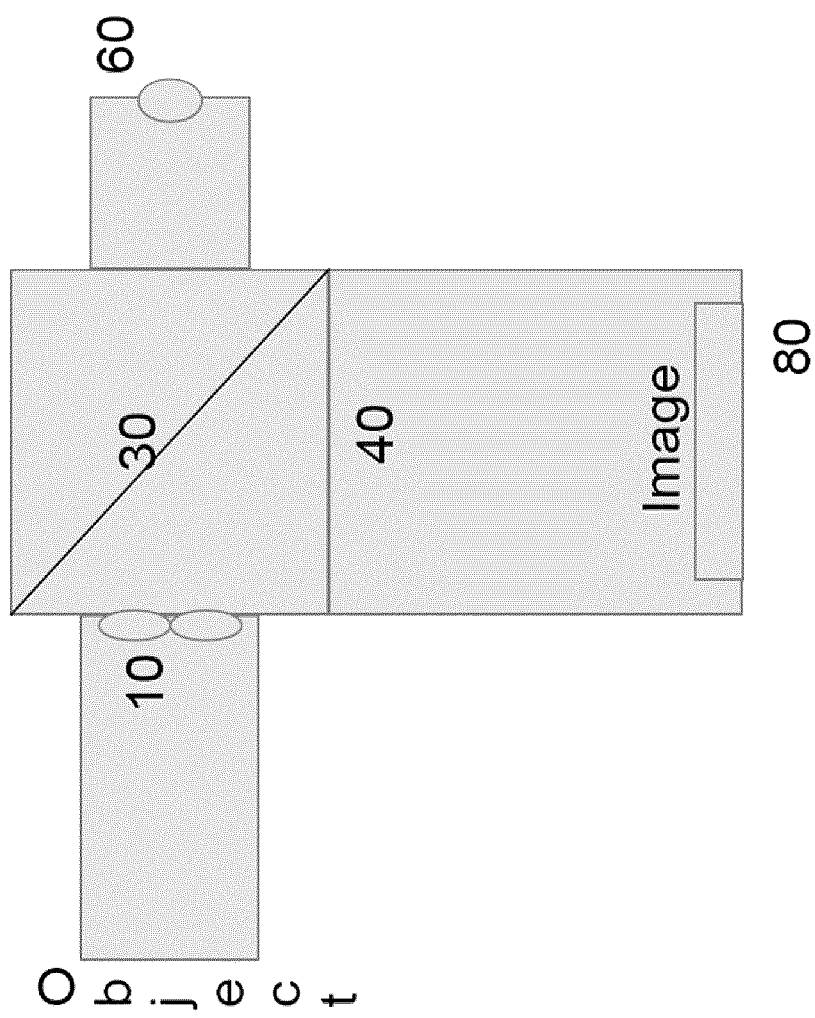

FIGS. 18A and 18B show different geometrical arrangements of the device. FIG. 18A shows the arrangement like those described in the embodiments above, in which the illumination light from light source 60 is reflected off a dichroic mirror 30 and transmitted to the object being examined by fiber bundles 10. The light emitted from the object passes back through the fiber bundles 10, is transmitted by the mirror 30 and passes through lens 40 toward detector 80. FIG. 18B shows an alternative arrangement where the illumination light from light source 60 is transmitted through the dichroic mirror 30 and into the fiber bundles 10, and the light returning through the fiber bundles 10 is reflected by the dichroic mirror toward the lens 40 and detector 80. This arrangement has a slight advantage for its compactness to fit in a small backpack that may be located on the back of a small animal subject, such as a mouse.

The following examples are set forth to aid in the understanding of the invention, and should not be construed to limit in any way the scope of the invention as defined in the claims which follow thereafter.

EXAMPLES

For an embodiment like that shown in FIG. 5, the following are examples of certain specific components that may be used. The coherent fiber bundle 510 consists of 13.5K single fibers, each with a core diameter of 8.2 µm. The diameter of the coherent bundle is 1 mm. In this example, the system is designed to allow for four such bundles to be imaged on the detector. The detector is an HD-CMOS detector, equivalent to a Webcam C615, produced by Logitech, Inc., Newark, Calif., with all lenses and filters removed. The images are transferred to the computer using a USB port and recorded using Amcap video software. An anti-reflection coated spherical lens in the visible regime, with a numerical aperture of 0.55 and a focal length of 4.6 mm is placed at a distance of 11.5 mm from the detector. An aperture of diameter 5 mm is placed at about 1 mm from the lens. The four fiber bundles are placed at 6.5 mm from the lens.

Not using a lens at the tip of the fiber bundles results in an image with the field of view of about 1 mm in diameter, and a resolution of better than 30 microns. Using a 1 mm half-ball lens attached to the face of the fiber bundle with no spacing between them results into a resolution of better than 30 microns. Using a GRIN lens with a 1.8 mm diameter and a pitch of 0.25 at 670 nm situated at 4.5 mm from the tip of the fiber bundle gives a field of view of greater than 400 microns with resolution better than 30 microns. Putting this lens at a distance of 7 mm from the coherent fiber bundle gives the image with a field of view of about 250 microns, with a resolution of better than 30 microns.

In some configurations one might require a magnification and resolution that needs the GRIN lens to be at a certain distance from the object. In such a situation one can use a spacing glass rod or a thin sheet of glass attached to the end of a hollow tube, which will then act as a glove to hold the GRIN lens at a distance from the object. The thin sheet will be touching the object and holding everything in place. This can be used in brain neural imaging if required. Using a 1 mm diameter GRIN lens with pitch of 0.23 at 800 nm at 3 mm distance from the tip of the coherent bundle gives a resolution of better than 30 microns.

For illumination a white LED is used, which is placed at the distance of 10 mm from an array of four microlenses each with a diameter of 1 mm and a focal length of 9 mm, positioned side-by-side to make a square of four lenses.

Instead of a dichroic mirror, a broadband visible 50:50 beamsplitter with size 1 mm×11 mm×11 mm reflects half of the white light into the set of fiber bundles and transmits the other half. The transmitted part gets absorbed by the matte black wall of the housing. The beamsplitter likewise sends only half of the light that is reflected back from the object towards the detector. The reason for replacing the dichroic mirror with the beamsplitter is to allow the transmission and reflection of a wide range of wavelengths.

To adapt this example for other imaging types described in the section above, the particular distances between the optical elements in this example may remain the same, while the illumination and detection are adapted for fluorescence, hyperspectral and polarization imaging. For example, for polarization imaging, one uses a quarter-wave plate and half-wave plate each about 300 microns thick, followed by a polarization beamsplitter cube of size 5 mm×5 mm×5 mm, in the space of 11.5 mm between the lens and detectors. The distance of the detector to the lens, which has a focal length 4.5 mm, is then reduced to make the optical path, which includes the glass of the polarization cube and the waveplates, which are equivalent to 11 mm in free space to form a focused image.

In another example, one uses a dichroic mirror that transmits wavelength ranges of 500 nm to 540 nm and 560 nm to 625 nm and reflects all other wavelengths. The illumination is by a flat-white LED, followed by a filter that transmits ranges of 450 nm to 490 nm and 540 nm to 555 nm. The emission filter allows the range of 500 nm to 530 nm and 570 nm to 610 nm. Such a configuration allows fluorescence imaging of two different colors, or protein markers.

For confocal and multi-photon imaging the device should change to the specifics or distances and focal lengths that are described in the section above for each of these imaging methods.

Figure 19B:
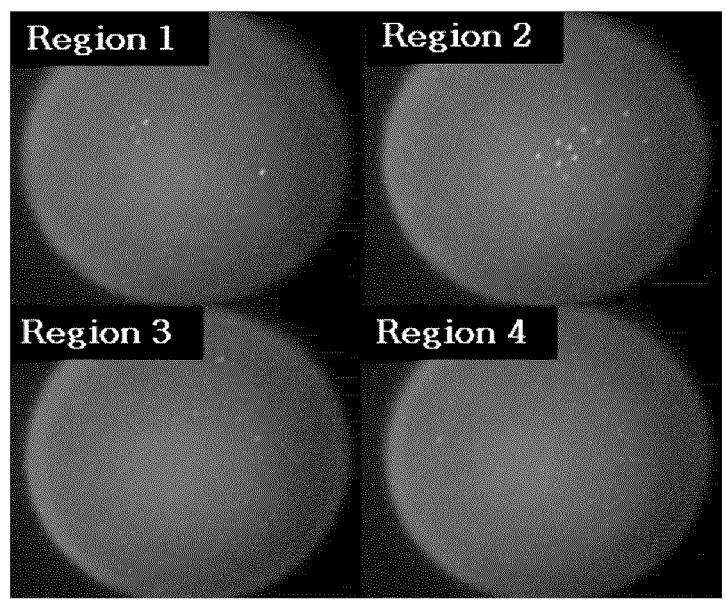
FIG. 19B is a graphical depiction of fluorescence images from four regions imaged with the present invention.

An artistic rendering of the example of the device used for examining a mouse is shown in FIG. 19A. The device is kept in a backpack 1905 that is worn by the mouse. The coherent fiber bundles 1910 are implanted into the mouse's brain and are fixed with dental cement. They then go in the backpack and connect to the optical components in the backpack. In order to see the collected images on a computer, one connects the electronics in the backpack to the USB or any other required port of the computer by connecting the wire to the electronics board through an opening 1903 in the backpack 1905. FIG. 19B shows the example of fluorescence imaging of the neurons of the mouse. The user can simultaneously see the neurons firing in four different brain regions while the mouse is moving about freely. One powerful application of the present invention is to use it in combination with optogenetics, such that one stimulates particular parts of the brain using optogenetics methods and observes the global effect of that particular simulation on a mammals sensory system, with single cell resolution, while the mammal is moving about.

Another powerful application of the device is for drug development and makes use of the fact that the device can simultaneously image various regions of the body of a small mammal. For example, one can implant one micro-objective 520 (FIG. 5) on the heart, two in two different regions of the brain and one in the spinal cord. A drug that is under development, such as a central nervous system drug, may then be given to the animal. The animal is then monitored to determine whether the drug is having the desired effect on the brain regions of interest, while simultaneously observing any side effects of the drug on the cardiovascular system and the regions of the central nervous system one does not want to affect.

While the foregoing invention has been described in some detail for purposes of clarity and understanding, it will be appreciated by one skilled in the art, from a reading of the disclosure that various changes in form and detail can be made without departing from the true scope of the invention in the appended claims.

The invention claimed is:

1. A multiple target optical imaging apparatus for providing optical imaging of a plurality of physically-separated imaging sites comprising:
   a light source;
   an optical detector; and
   a plurality of coherent fiber bundles each comprising a plurality of optical fibers, said optical fibers of each fiber bundle being configured to convey light generated by the light source from a proximal end of the bundle to a distal end of the bundle, wherein each bundle is configured to have its distal end positioned adjacent to a different one of the imaging sites, and wherein said optical fibers of each bundle are also configured to convey an optical signal from a respective imaging site from the distal end of the bundle to the proximal end of the bundle, the optical signal being detected by the optical detector.

2. An apparatus according to claim 1 wherein the optical signal from each fiber bundle is directed to a different spatial region of a detection surface of the detector.

3. An apparatus according to claim 1 wherein the detector detects all of the optical signals simultaneously.

4. An apparatus according to claim 1 wherein the imaging sites comprise different imaging locations on a biological subject.

5. An apparatus according to claim 4 wherein the plurality of imaging sites correspond to a plurality of different biological systems of the subject.

6. An apparatus according to claim 1 further comprising a battery for powering the light source and detector.

7. An apparatus according to claim 1 further comprising a wireless transceiver for communicating data collected by the detector to a remote location.

8. An apparatus according to claim 1 wherein at least one of the fiber bundles comprises a magnification element that provides magnification of the optical signal received from the respective imaging site for that bundle.

9. An apparatus according to claim 1 further comprising a wavelength dispersive element that separates the optical signal from at least one of the fiber bundles into discrete wavelength ranges.

10. An apparatus according to claim 1 further comprising a polarization-dependent filter that filters the optical signal of at least one of the fiber bundles.

11. An apparatus according to claim 1 further comprising a dichroic mirror that separates light at a wavelength of the light source from light at a wavelength of the optical signal of at least one of the fiber bundles.

12. An apparatus according to claim 1 further comprising a beamsplitter that separates light passing through one or more of the fiber bundles in a wavelength-independent manner.

13. An apparatus according to claim 1 further comprising a plurality of lenses each associated with a different one of the fiber bundles.

* * * * *